United States Patent [19]

Ladouceur

[11] Patent Number: 5,894,061
[45] Date of Patent: *Apr. 13, 1999

[54] DIFFUSION THROUGH A MEMBRANE ASSAYING APPARATUS AND METHOD

[76] Inventor: Cynthia A. Ladouceur, 7857 Bastille Pl., Severn, Md. 21144

[*] Notice: This patent is subject to a terminal disclaimer.

[21] Appl. No.: 08/605,305

[22] Filed: Jan. 29, 1996

Related U.S. Application Data

[63] Continuation of application No. 08/173,854, Dec. 23, 1993, abandoned, and a continuation of application No. 07/928,121, Aug. 19, 1992, abandoned, is a continuation of application No. 08/371,711, Jan. 12, 1995, Pat. No. 5,525,475.

[51] Int. Cl.[6] .................. G01N 33/536; G01N 33/537; G01N 33/558
[52] U.S. Cl. .............. 435/7.9; 73/52; 73/863.23; 210/634; 210/640; 210/641; 422/58; 422/60; 422/61; 422/70; 435/7.92; 435/7.93; 435/7.94; 435/7.95; 435/287.1; 435/287.2; 435/288.2; 435/807; 436/164; 436/165; 436/171; 436/172; 436/177; 436/178; 436/514; 436/805
[58] Field of Search .................. 73/52, 863.23; 210/634, 640, 641; 220/502, 529; 422/58, 60, 61, 70, 99–102; 435/7.9, 7.91–7.95, 12, 32, 287.1, 287.2, 288.2, 807, 808, 810, 970, 973, 975; 436/164, 165, 171, 172, 177, 178, 536, 538, 514, 805, 807, 808, 809, 910

[56] References Cited

U.S. PATENT DOCUMENTS

| | | | |
|---|---|---|---|
| 3,948,606 | 4/1976 | Johnson | 424/1.5 |
| 4,266,021 | 5/1981 | Nylen et al. | 435/14 |
| 4,663,126 | 5/1987 | Gould et al. | 422/55 |
| 4,865,813 | 9/1989 | Leon | 422/44 |
| 5,525,475 | 6/1996 | Ladouceur | 435/7.9 |

FOREIGN PATENT DOCUMENTS 2245797  3/1973  Germany .

*Primary Examiner*—Christopher L. Chin
*Attorney, Agent, or Firm*—John F. Moran; John Callaghan

[57] ABSTRACT

The diffusion through a membrane assaying apparatus and method facilitates rapid detection of small or larger molecular weight substances such as hazardous wastes, toxic chemicals or the like by using a semipermeable membrane having a predetermined molecular weight cutoff. The semipermeable membrane is provided as part of a container having a removable barrier which facilitates control of diffusion through the membrane. The assaying method includes the use of a reaction mechanism for detection of a predetermined substance. The reaction mechanism includes one or more reagents which are designed to either react or compete for a substance for which assaying is being performed. By selecting the proper reagents and molecular weight cutoff of the semipermeable membrane, the presence or absence of a reaction such as a color change or production of vapor provides indication whether the substance being assaying for is present in the test sample.

5 Claims, 20 Drawing Sheets

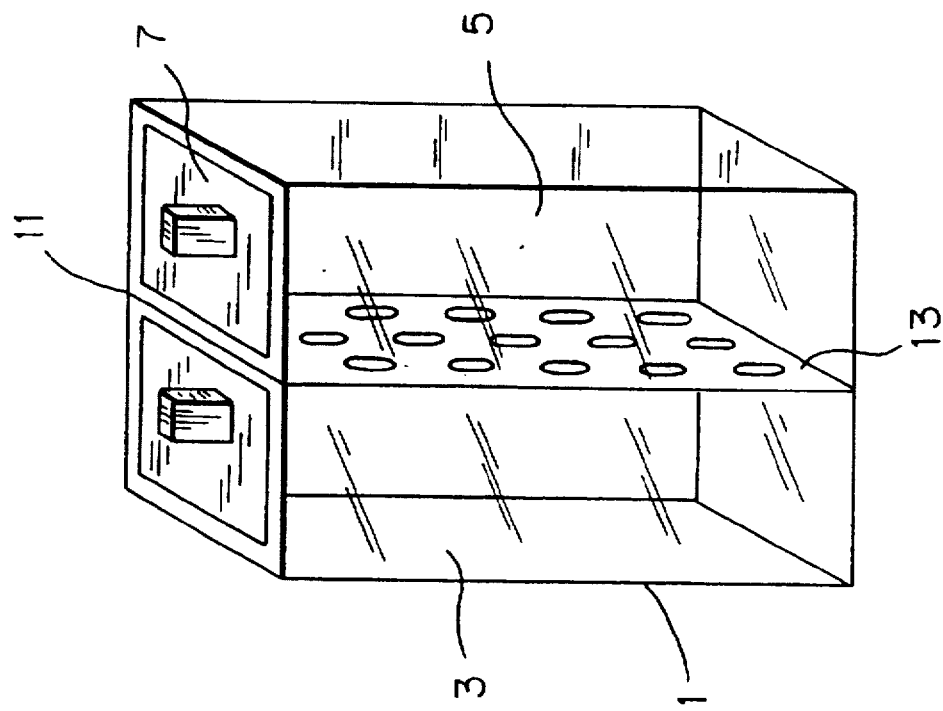
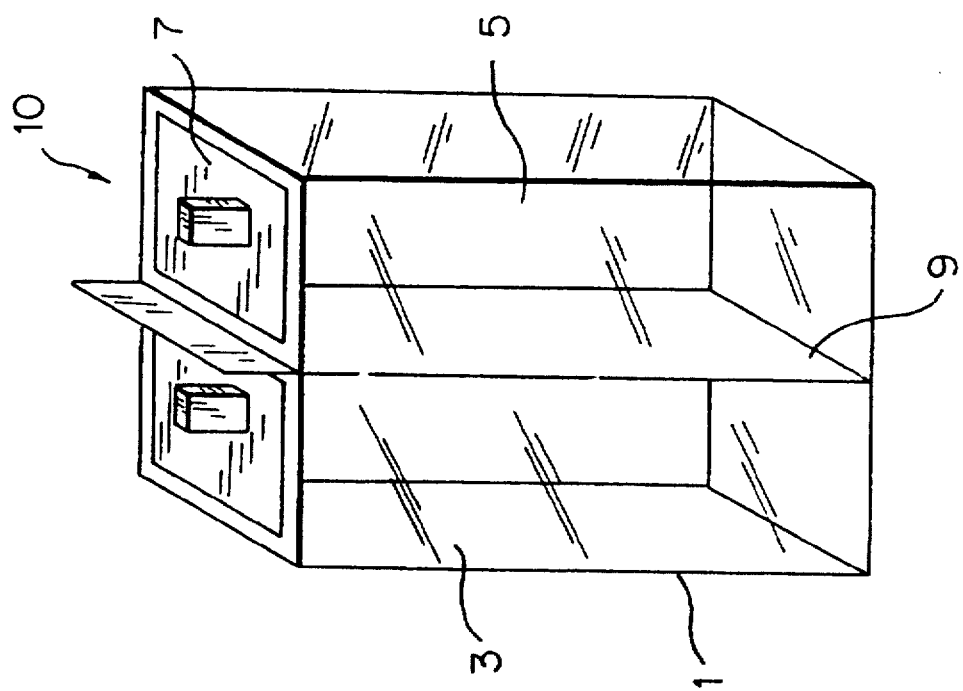

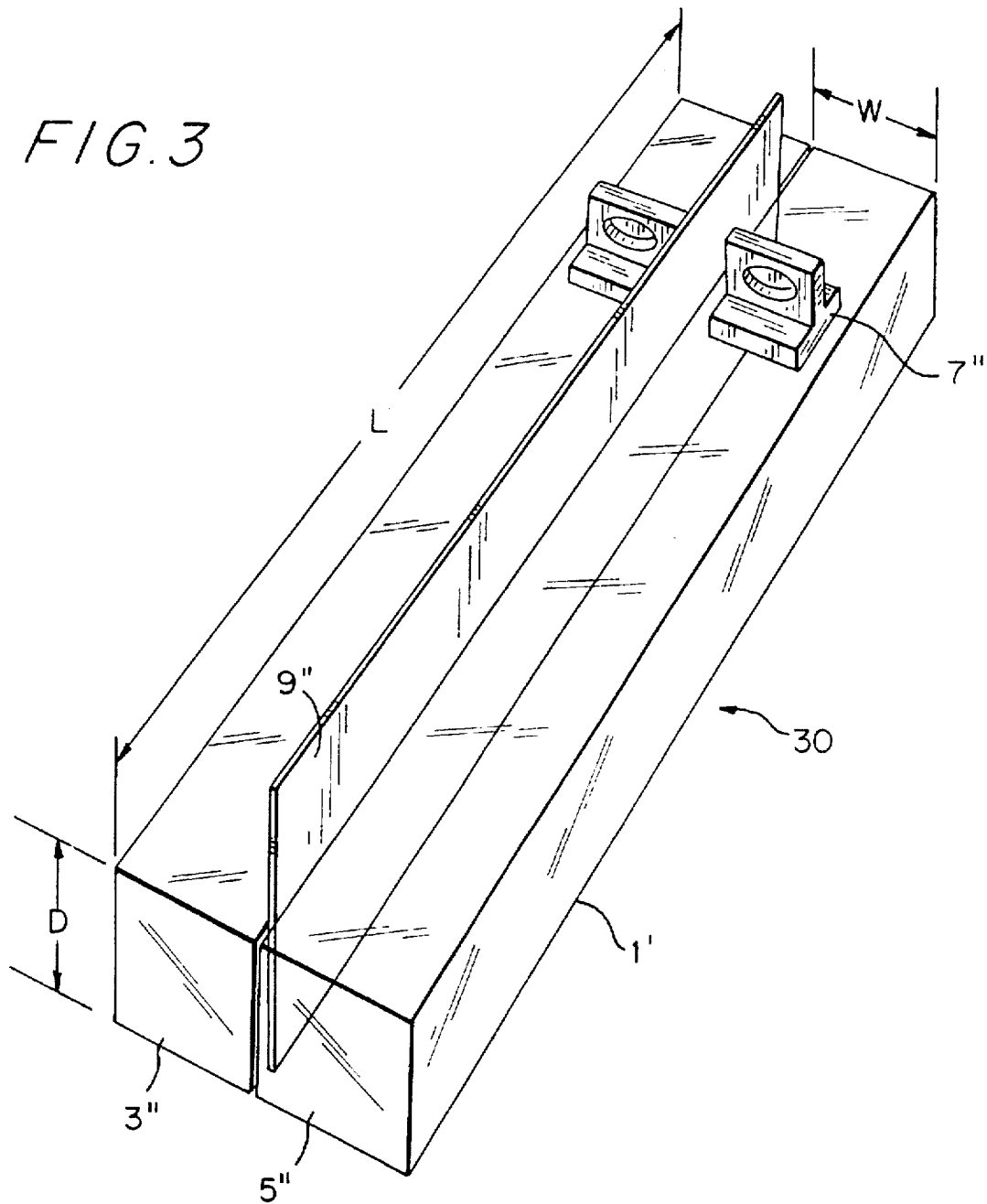

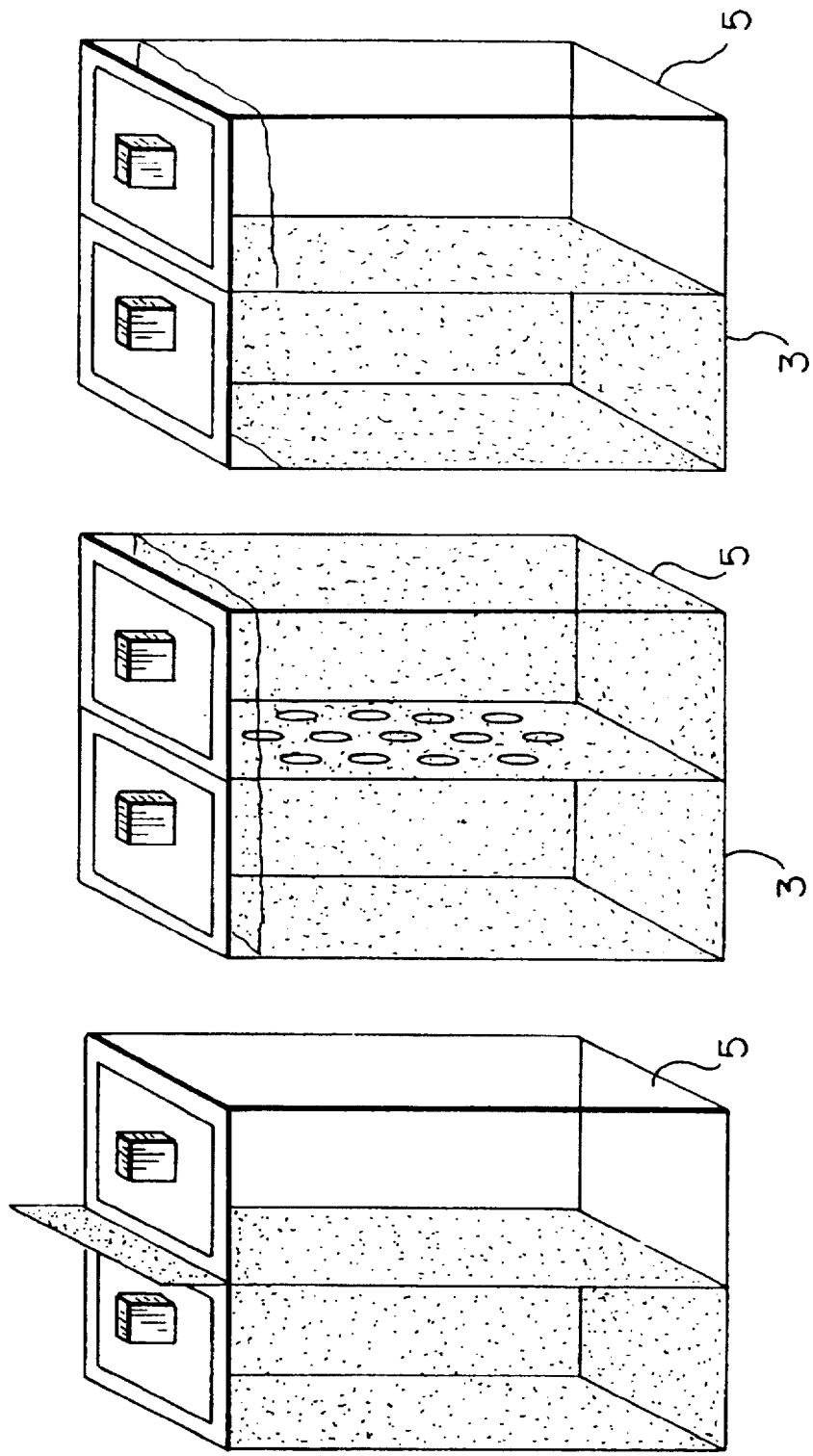

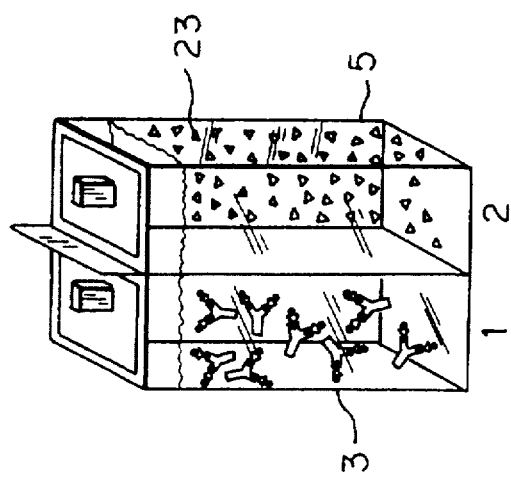
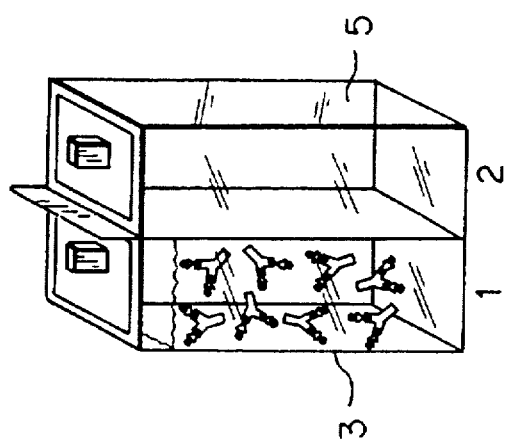
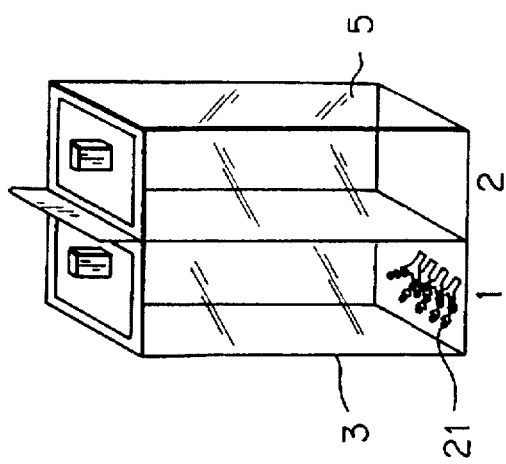

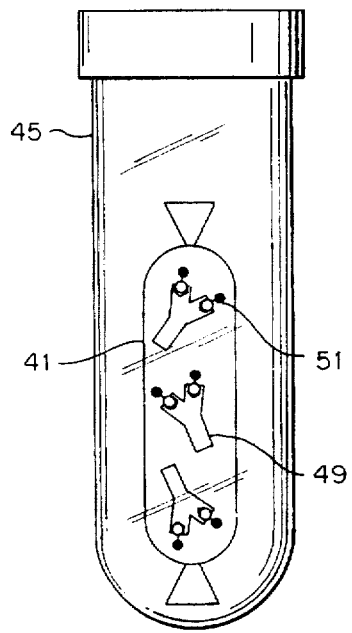 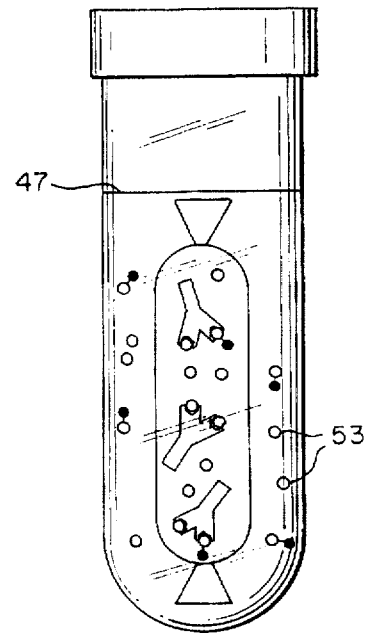 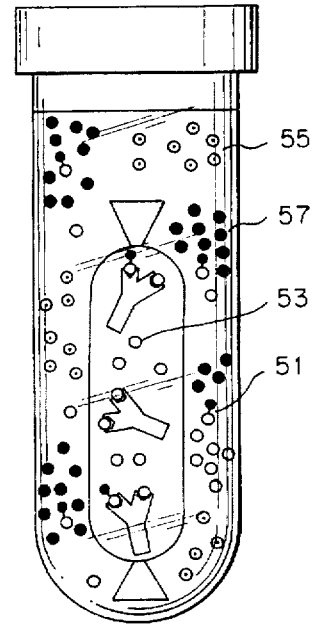

```
┌─────────────────────────────────────────────────────────┐
│ ADD TEST SAMPLE CONTAINING BACTERIA/FUNGI AND           │
│ THE ANTIBODY-ENZYME CONJUGATE TO THE BAG. BAG IS        │
│ SECURED BY CLAMPING AT BOTH ENDS.                       │
│              SHAKE FOR 1-2 MINUTES.                     │
└─────────────────────────────────────────────────────────┘
                            │
                            ▼
┌─────────────────────────────────────────────────────────┐
│     PLACE BAG IN A PETRI DISH CONTAINING ENZYME         │
│                      SUBSTRATE.                         │
│                  SHAKE FOR 1 MINUTE.                    │
└─────────────────────────────────────────────────────────┘
                            │
                            ▼
┌─────────────────────────────────────────────────────────┐
│ REMOVE THE BAG FROM THE PETRI DISH TO STOP              │
│ MOLECULES FROM MIGRATING THROUGH THE SEMI-              │
│                  PERMEABLE MEMBRANE.                    │
│                                                         │
│ LITTLE OR NO ENZYME IS PRESENT TO REACT WITH            │
│ SUBSTRATE AND VOLATILE REACTION PRODUCTS                │
│ (VAPORS) ARE NOT PRODUCED. USE VAPOR-DETECTING          │
│ EQUIPMENT TO DEMONSTRATE THAT VAPORS ARE ABSENT         │
│ (FOR A POSITIVE TEST SAMPLE SUCH AS THIS). FOR A        │
│ NEGATIVE TEST SAMPLE, VAPORS WOULD BE PRESENT.          │
└─────────────────────────────────────────────────────────┘
```

FIG. 14

F/G. 17A
F/G. 17B
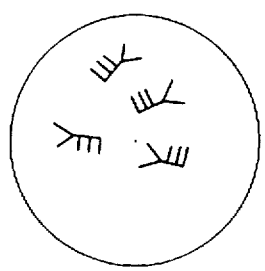
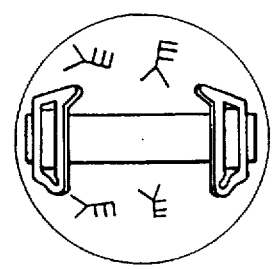
F/G. 17C
F/G. 17D
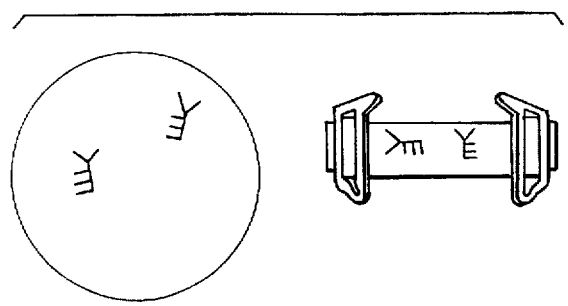
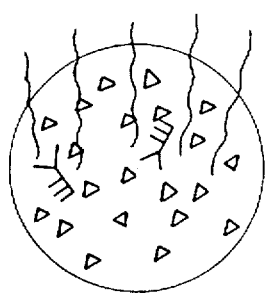

DIFFUSION THROUGH A MEMBRANE ASSAYING APPARATUS AND METHOD

This application is a continuation of Ser. No. 08/173,854 filed Dec. 23, 1993 and Ser. No. 07/928,121, filed Aug. 12, 1992, both now abandoned, and a division of Ser. No. 371,711, filed Jan. 12, 1995, now U.S. Pat. No. 5,525,475.

FIELD OF THE INVENTION

The present invention is directed to a diffusion through a membrane assaying apparatus and method, and in particular, a portable container or a membrane in the form of a container which facilitates the rapid detection of small or large molecular weight substances such as hazardous wastes, pesticides, toxic chemicals, chemical warfare agents, proteins from infectious organisms or the like.

BACKGROUND OF THE INVENTION

In the prior art, various methods and devices have been proposed for assaying various substances. U.S. Pat. No. 4,770,853 to Bernstein discloses a device for self-contained solid-phase immunodiffusion assay comprising a sample collector, a tube with compartmentalized reagents and a ligand receptor capture membrane filter area. The sample collector is pushed through seals in the device and is mixed with reagent, and then pushed into a ligand receptor reaction area. A tip of the sample collector contacts diffusible membranes and transfers the reactants to a capture membrane for visualization of a ligand receptor reaction by a viewer.

U.S. Pat. No. 4,818,677 to Hay-Kaufman et al. discloses methods and a kit for performing immunoassays. The kit includes a reaction cell having a micro-porous membrane and an absorbent capable of drawing a liquid sample through the membrane. Analyte in the sample is immobilized, typically by immunoadsorption, and the immobilized analyte may then be visualized using conventional signal producing systems, such as color, fluorescence and luminescent systems.

U.S. Pat. No. 5,043,260 to Jauregui discloses a perfusion device to grow and maintain hepatocytes including a chamber having a perfusion inlet and a perfusion outlet. A semipermeable membrane in the chamber defines separate perfusion and hepatocyte compartments, the hepatocytes therein being attached via oligosaccharide-lectin recognition linkage to a biopolymer support in the hepatocyte compartment.

The prior art also teaches immunochemically-based methodologies for the detection of small or large molecular weight substances. Exemplary of these methodologies include radioimmunoassay, enzyme-linked immunosorbent assay, enzyme multiplied immunoassay, enzyme immunoassay, fluorescent immunoassay, nephelometric inhibition immunoassay, hemagglutination inhibition, microbiologic assay, free radical assay technique—also called spin immunoassay, liposome immunoassay and potentiometric immunoassay.

U.S. Pat. Nos. 5,002,871 and 5,037,741 to Iacobucci disclose a membrane method for the enzymatic synthesis of peptides. The method employs a membrane permeable to uncharged peptides but impermeable to charged molecules. The enzymatic method provides a process for the safe, economical and efficient synthesis and purification of peptides and derivatives thereof, and the efficient use of enzymes and the means to affect the synthesis on a continuous basis.

Disadvantages of currently used immunoassays include difficulty when using under field conditions, expensive, difficult to perform without training, time consuming and the requirement of multiple reagents, many of which can undergo degradation and, thus, interfere with test results. In view of the deficiencies in prior art detection methodologies, a need has developed to provide a rapid, portable, easy to use, inexpensive and versatile assaying apparatus and method.

In response to this need, the present invention provides an assaying apparatus and method which overcomes the deficiencies in the prior art. The inventive assaying apparatus and method provides results within a few minutes, requires a small number and small volume of reagents, utilizes simple chemical reactions to perform given assays, provides long shelf life reagents and provides easily interpreted assay results.

SUMMARY OF THE INVENTION

It is accordingly a first object of the present invention to provide an assaying apparatus and method utilizing diffusion through a membrane.

It is another object of the present invention to provide an assaying apparatus that provides results in a short period of time, is portable for field environment use, is simple to use and is inexpensive.

A further object of the present invention is to provide an assaying apparatus and method of assaying which requires a small number and small volume of reagents, thereby decreasing assaying unit costs.

Another object of the present invention is to provide an assaying apparatus and method which offers easily interpreted results for assay determination.

Other objects and advantages of the invention will be apparent as the description thereof proceeds.

In satisfaction of the foregoing objects and advantages, in a first embodiment, the present invention comprises an assaying apparatus for detecting a wide range of molecular weight substances including a container having first and second chambers therein. The first and second chambers are separated by a removable non-permeable barrier and an adjacent semipermeable membrane. The semipermeable membrane is selected having a molecular weight cut off value in accordance with the particular substance for which assaying is being performed. The first and second chambers each have an opening and a cap adapted to close each opening. During assaying, the non-permeable barrier is removed to permit diffusion through the semipermeable membrane and between the two chambers.

Various reagents are provided for addition to each of the chambers to permit assaying a sample for determination of a particular molecular weight substance. The chambers may be configured to facilitate visual detection of reactions during assaying and can include caps with indicia thereon to further facilitate particular assaying methods.

In an alternative embodiment, the semipermeable membrane is provided in a container form. In this embodiment, the semipermeable membrane container is utilized with a reaction vessel and reagents for performing the various assaying methods. In one embodiment, the reaction vessel may be a closed vessel wherein the vessel cap includes provision for storing reagents. The semipermeable membrane container can also be utilized with an open reaction vessel such as a Petri dish.

The assaying apparatus can be used with a variety of reagents for detection of both small and large molecular weight substances. In one mode of the inventive assaying method, color changes, production of vapors or intensity of color changes or vapor production are utilized to facilitate detection of a given substance. During the assaying methods, the molecular weight cut off value of the semipermeable membrane controls diffusion across this membrane. Thus, and depending upon the size of the reagents used, a user can select the reagents in conjunction with the semipermeable membrane molecular cut off weight size to identify particular molecular weight substances.

In one particular mode of assaying, an antigen to be tested for is labeled with a labeling agent. The labeled antigen is associated with a particular antibody to establish a given molecular weight substance. During assaying, and if antigens are present in a test sample, the antigens replace the labeled antigens on the antibodies. Since the labeled antigens are small enough in size to diffuse through the semipermeable membrane, the presence of the antigen can be detected as a result of the labeled antigen diffusion and producing a corresponding color change.

In an alternate mode of assaying, an enzyme substrate system is provided wherein the enzyme acts as the labeling agent. By controlling diffusion with the semipermeable membrane and the size of the substance which the enzyme labels, the reaction between the enzyme and substrate, either as a color change or vapor production, is controlled to indicate detection of a given substance.

Besides selecting particular reagents for the inventive assaying method, the reagents and a sample to be tested for detection of a substance having a predetermined molecular weight can be combined in a predetermined sequence with the containers as described and reaction vessels to obtain an assaying result by diffusion through the semipermeable membrane of select reagents.

BRIEF DESCRIPTION OF DRAWINGS

Reference is now made to the drawings accompanying the application wherein:

FIG. 1a depicts a first embodiment of the inventive assaying apparatus with the non-permeable barrier intact;

FIG. 1b shows the apparatus depicted in FIG. 1a with the non-permeable barrier removed, thus exposing the semipermeable membrane;

FIG. 3 shows a perspective view of another configuration of the assaying apparatus depicted in FIG. 1;

FIGS. 4a–4c show the assaying apparatus of FIG. 1 in exemplary modes of use;

FIGS. 5a–5e are diagrammatic representations of an exemplary reaction sequence using the assaying apparatus of FIG. 1;

FIGS. 9A, 9B, 9C shows a diagrammatic representation of an exemplary reaction sequence using the apparatus and key depicted in FIG. 8;

FIGS. 11a–11d show a diagrammatic representation of a reaction sequence utilizing the embodiment depicted in FIG. 10a;

FIG. 14 is a flowchart describing the reaction sequence for FIGS. 13a–13c;

FIGS. 17a–17d show another diagrammatic representation of a reaction sequence when the presence of less vapors indicates a negative reaction.

DESCRIPTION OF THE PREFERRED EMBODIMENTS

Figure 2:
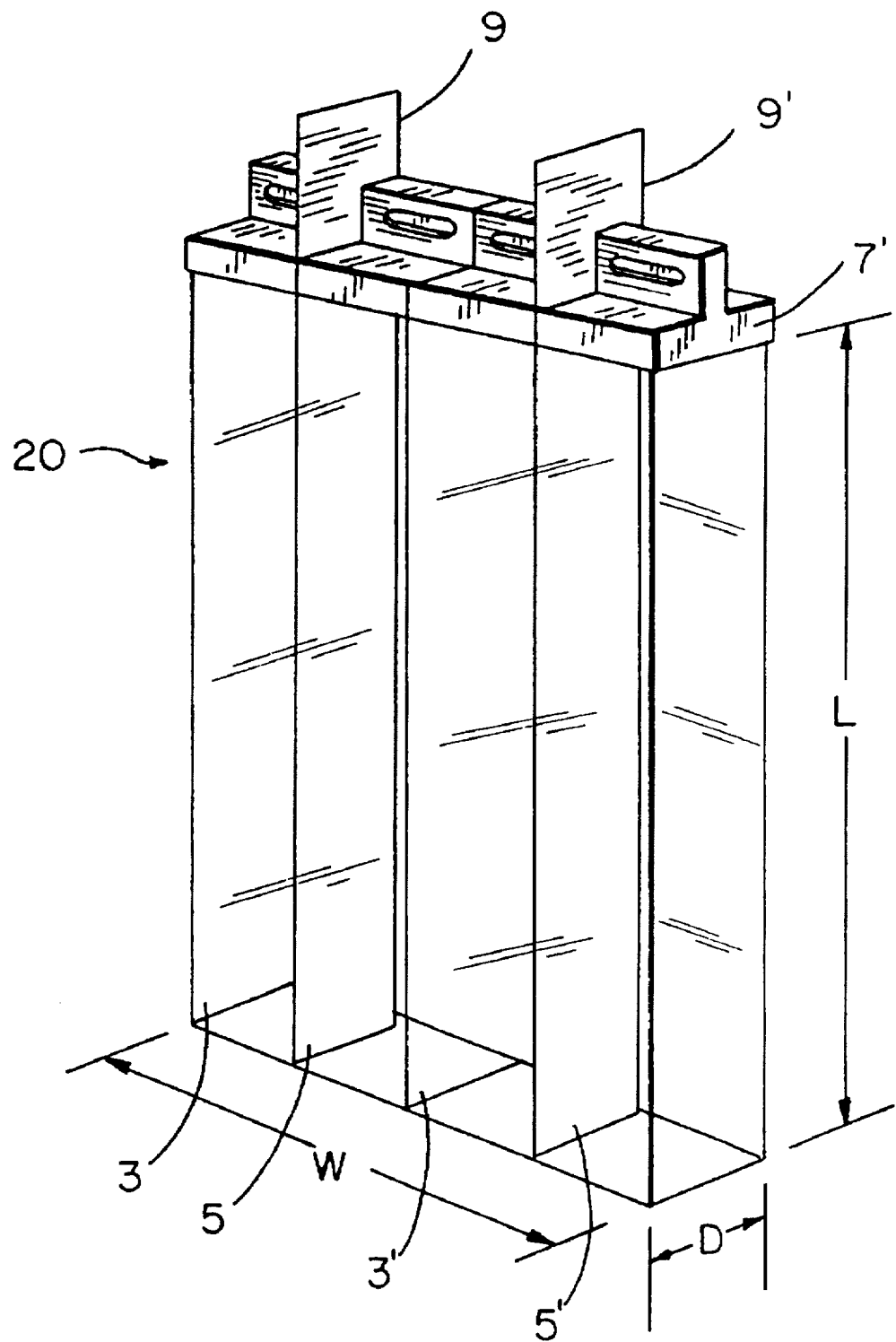
FIG. 2 shows a perspective view of a multiple chamber assaying apparatus.

The inventive assaying apparatus and method utilizing diffusion through a membrane solves the prior art problem of detecting both small and large molecular weight substances in a single assaying apparatus. The inventive assaying apparatus is capable of detecting small molecular weight substances such as chemical warfare agents, drugs (both therapeutic and those of abuse), hormones such as progesterone, and toxins, e.g., T-2 toxin. The inventive assaying apparatus and method also includes capability of detecting large molecular substances including a variety of proteinaceous substances from infectious organisms, e.g., bacteria, fungi and parasitic organisms, and antibodies directed against these substances.

The inventive assaying apparatus and method includes a wide variety of applications. For example, the assaying apparatus can be used to identify samples that contain life-threatening chemicals such as warfare agents by members of the military. Moreover, rapid detection of drugs in biological samples such as urine can be achieved using the inventive assaying apparatus and method. Drugs can be constantly monitored for therapeutic use or when people or animals, e.g. race horses, have taken or have been given drugs of abuse.

The assaying apparatus and method may be used to determine hormone levels in body fluids to monitor patients, monitor athletes and monitor hormone levels for ovulation determination in women. The capability of detecting toxins makes the inventive assaying apparatus useful for all branches of the military and in medical related applications.

With reference now to FIGS. 1a and 1b, a first embodiment of the diffusion through a membrane (hereinafter DITAM) apparatus is generally designated by the reference numeral 10 and is seen to include a handheld transparent container 1 with first and second chambers, 3 and 5, respectively. The container 1 can be constructed from polystyrene or another optically clear and transparent material such as glass. With reference to FIG. 1a, each of the chambers 3 and 5 have a cap 7 which covers an opening in the respective chambers. Disposed between chambers 3 and 5 is a removable non-permeable barrier 9.

With reference to FIG. 1b, the non-permeable barrier 9 is removable from the container 1 via the slot 11 in a top portion thereof. Once the non-permeable barrier 9 is removed, a semipermeable membrane 13 is exposed, the semipermeable membrane being positioned between chambers 3 and 5. The semipermeable membrane is not removable from between chambers 3 and 5.

The molecular weight cutoff (hereinafter "m.w.c.o.") of the membrane 13 can be varied depending on the substance to be tested for. For example, the DITAM apparatus used to test for small molecular weight substances would utilize semipermeable membranes which have a relatively small pore size. Conversely, the DITAM apparatus used to test for large molecular weight substances would utilize semipermeable membranes which have a relatively large pore size. Although a variety of membranes can be employed, dialysis-type membranes are the most useful. This is due to the fact that molecules can easily migrate through the membrane when an individual is gently shaking the apparatus from side to side. Other membranes can be employed, but positive or negative pressure may be required for the molecules to traverse the membrane. For example, the apparatus can be reconfigured for use with a vacuum system if the membrane type requires the use of a vacuum for the molecules to migrate through the pores. Since this device was intended for field use, the use of a vacuum system with the apparatus is not desirable. Additional details and examples of actual membranes used for each embodiment of the DITAM apparatus are discussed hereinafter.

The caps can be produced from a colored material. If desired, caps can be produced in many different colors. Cap color may be used to differentiate an apparatus that is used for a particular test. For example, a DITAM apparatus with an orange cap can be reserved to test for substance "A". A DITAM apparatus with a blue cap can be reserved to test for substance "B". Caps can also be transparent and devoid of coloring. All of the instructions for performing a DITAM assay can be printed on one or two sides of the apparatus.

With reference now to FIG. 2, a four-chambered apparatus is designated by the reference numeral 20 and is seen to include a first pair of chambers 3 and 5 separated by a first non-permeable barrier 9 and a second pair of chambers 3' and 5' separated by a non-permeable barrier 9'. In this configuration, a control sample can be tested in chambers 3 and 5 with a test sample assayed in chambers 3' and 5'. As described above, the non-permeable barriers 9 and 9' of the four-chambered apparatus are removed by lifting upwardly to expose the semipermeable membranes described previously. The four-chambered apparatus 20 also includes caps 7' which are also removable to permit access to the various chambers.

The four-chambered apparatus is shown having a length designated by "L", a depth "D" and a width "W". Exemplary dimensions for the four-chambered apparatus 20 include a length of 44 mm, depth of 12 mm and a width of 51 mm. Of course, the four or two chambered apparatus can be made with different dimensions to accommodate larger or smaller reagent and sample volume sizes. Further, a different size may also be constructed for use with a particular mechanical optical density reading device.

When viewing a solution in chambers 3' and 5' of the four-chambered apparatus 20, a viewer can look at the apparatus through a front view, or with the cap removed, through a top view. Given exemplary dimensions of a 12 mm depth and a 44 mm height, viewing a reaction solution through the front view makes the solution appear lighter. In contrast, when the reaction solution is viewed through a top view with a path length of 44 mm, the solution appears darker. The difference in path lengths allows for greater test sensitivity when viewing along a longer path length without the need for a mechanical reading device.

An elongated version of the apparatus disclosed in FIGS. 1a and 2 is depicted in FIG. 3. The elongated version allows an individual to view a colored reaction solution through a longer path length, and the color of the reaction solution appears to be darker. Thus, it is easier for an unaided eye to visualize test results. The DITAM apparatus depicted in FIG. 3 is generally designated by the reference numeral 30 and is seen to include a container 1' divided into chambers 3" and 5" by non-permeable barrier 9". The caps 7" are disposed on a top surface of each of the chambers such that the test apparatus rests on a surface opposite a surface containing the openings for the caps 7". In the apparatus 30, exemplary dimensions include a length of 88 mm, a depth of 12 mm and a width of 25 mm. Again, the apparatus 30 can be made with different dimensions to accommodate larger or smaller reagent and sample volume sizes. A different size may also be constructed for use with a particular mechanical optical density reading device.

As set forth above, the non-permeable barrier 9" is removed by lifting upwardly to expose the semipermeable membrane positioned between chamber 3" and 5".

It should be understood that the configuration, sizes and shapes of the assaying apparatus 10, 20 and 30 are merely exemplary and, as such, may be constructed in different sizes and shapes to accommodate the needs of a user.

In its simplest form, the DITAM assay requires the following reagents: antibody molecules which recognize a specific antigen (or several different antigens), specific antigens labeled with chromophores or fluorophores, and a buffer solution. The test sample may contain antigen or it may be devoid of antigen. The antigen is the specific substance that is being tested for. This antigen (or several antigens) are specifically recognized by the antibody molecules that are employed in the assay. In its simpleest form, the DITAM assay utilizes a chromophore or fluorophore to label the antigen and to indicate a positive or negative test result. FIGS. 4A–4C illustrate the use of fuchsin red is as a label for antigens. Prior to testing, the solution in chamber 3 of the DITAM apparatus is shown as shaded (FIG. 4A), but is pink in actual use. When a test is completed, a negative reaction (no antigen in test sample) appears shaded in chamber 3 and relatively clear in chamber 5 (FIG. 4C). When a test is completed, a positive reaction (antigen in test sample) appears light pink in both chambers 3 and 5 (FIG. 4B).

Several different labeling substances may be used in place of the chromophores or fluorophores. A variety of enzymes may be used to label the antigens. If these are employed, an extra step is added to the test; and the appropriate enzyme-substrate solution is required. If used, the cap of the apparatus could be configured to enable the storage of the enzyme-substrate solution in the cap. The reaction of enzyme and enzyme-substrate solution may produce a colored reaction product. Alternatively, the reaction of enzyme and enzyme-substrate solution may produce vapors; and these vapors could be detected by a user with a chemical vapor detection device.

All reagents can be supplied in lyophilized form and can be reconstituted with a buffer solution immediately prior to performing an assay. In lyophilized form, the DITAM apparatus and the assay reagents can be stored at 4° C. or a lower temperature until ready for use. Degradation of these reagents will be halted or delayed substantially if stored properly. A stabilizer may also be added to the chamber to prolong the shelf life of the reagents. Thus, reagents do not degrade as rapidly when exposed to warm environments.

The test sample may be a liquid, i.e., contaminated water, saliva, serum or urine. Alternatively, solid test samples, i.e., contaminated dust particles, can be concentrated on cotton swabs and placed in test tubes along with a buffer solution. This process applies to all of the versions of the DITAM Assay.

The direction for performing a DITAM Assay will now be described. Prior to performing a DITAM Assay, an individual must select a DITAM apparatus which contains a semipermeable membrane with the appropriate pore size or molecular weight cutoff (m.w.c.o.). This membrane is discussed hereinafter. The caps are removed and reinserted as needed to add reagents to the chambers. Lyophilized reagents are reconstituted with a buffer solution or with 0.85% saline immediately prior to use. Alternately, an individual may reconstitute the reagents in several apparatus on the morning that the assays are to be performed. In this manner, one step is eliminated when assays are performed in the field or in the lab. Reconstitution of reagents several days in advance is not recommended since this may accelerate degradation of the reagents.

When an individual is ready to perform a DITAM assay, the test sample is added to chamber 5 of the apparatus; and the nonpermeable barrier is removed by lifting upwards. The individual then shakes the DITAM apparatus to allow smaller molecules to diffuse through the semipermeable membrane. After 2–3 minutes, the individual observes the apparatus for color changes in both chambers. This can be accomplished with the unaided eye or a small spectrophotometer. For field use, the former method of observation is preferred. Color in chamber 5 indicates the presence of antigen in the test sample. One type of color change that may be observed if a chromogen such as fuchsin red is used as a label for antigens is various shades of pink. The intensity of the color is dependent on the amount of chromogen on each side of the membrane.

Using a four-chambered apparatus as shown in FIG. 2, the two chambers, 3' and 5', can be used as a control for comparison with chambers 3 and 5 to assay a test sample. In this manner, chambers 3 and 5 should indicate a negative reaction (no antigen in the test sample) or a positive reaction (antigen in the test sample) with the two chambers, 3' and 5', illustrating a positive reaction or antigen present in the control sample. Although a chromogen such as fuchsin red has been described above for indicating the presence of an antigen, other indicating agents such as fluorescein may be used as a label for antigens. Using fluorescein, the reaction solutions appear as various shades of yellow. Again, when viewing for color changes using the assaying apparatus, viewing along a top view gives the appearance of a darker solution which is easier to visualize with an unaided eye.

With reference now to FIGS. 5A–5F, a diagrammatic representation of an exemplary reaction sequence for the DITAM assay will now be described. Once the correct DITAM apparatus is selected, the reactions can proceed.

Lyophilized antigen-chromogen (chromophore) conjugates bound to antibody molecules or antigen-fluorophore conjugates bound to antibody molecules 21 are placed in chamber 3 of the apparatus, (FIG. 5A). Reconstitution is accomplished by adding a buffer solution or 0.85% saline to chamber 3, and the molecules go into the solution (FIG. 5B). The solution becomes colored due to the presence of the chromophore or fluorophore. Many different colored solutions are possible depending on the color of the chromophore or fluorophore. For example, fuchsin red produces a pink colored solution. The intensity of the color is directly dependent on the concentration of fuchsin red in the solution. Fluorescein produces a yellow colored solution; and again, the intensity of the color is directly dependent on the concentration of fluorescein in the solution. Ideally, for field testing, it is desirable to utilize a sufficient quantity of the chromophore or fluorophore to enable the visualization of the colored solution with the unaided eye. If this not possible, a hand-held spectrophotometer may be required to detect the color changes during the course of the reactions.

The test sample is added to chamber 5 (FIG. 5C). A liquid sample may be tested, and this sample may or may not contain the antigen to be tested for. In the illustration, the antigen 23 is present in the test sample. If a solid test sample is added to chamber 5 of the apparatus, then a buffer solution or 0.85% saline must be added to chamber 5 in order to have the test sample go into solution. The nonpermeable barrier is removed by lifting upwards. This barrier may be removed completely; or it may be elevated to the level of the caps so that the barrier can be reinserted at a later time.

Figure 5F:
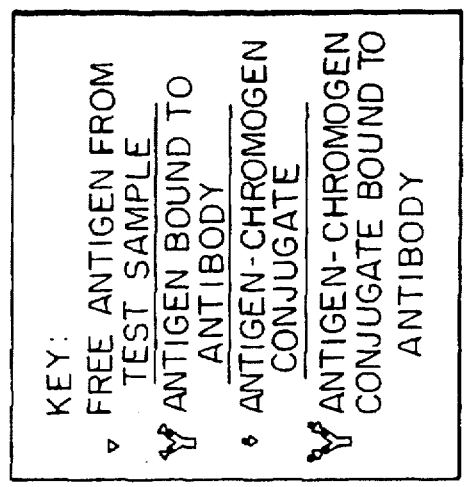
FIG. 5f is a key identifying substances used in the reaction sequence depicted in FIGS. 5a–5e.
Figure 5E:
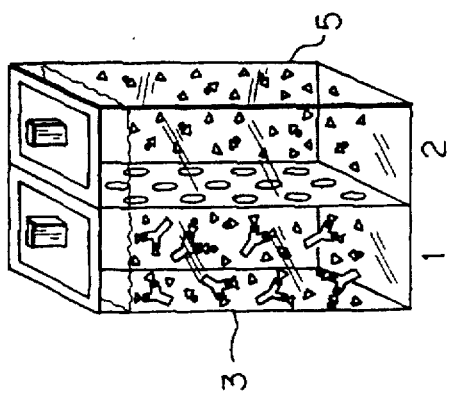
Figure 5D:
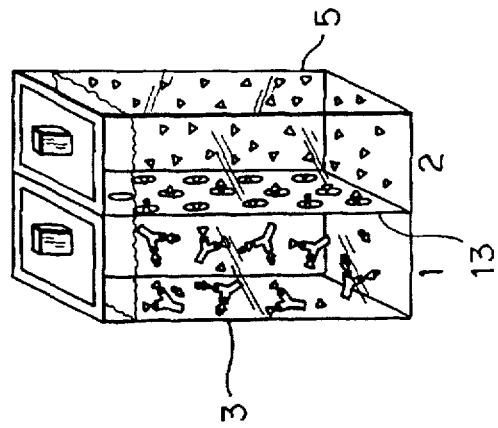

Once the nonpermeable barrier is removed, the permanently affixed semipermeable membrane is exposed, (FIG. 5D). The semipermeable membrane must have a m.w.c.o. that prohibits the antibody molecule from crossing from chamber 3 to chamber 5. The membrane must also have a m.w.c.o. that enables the antigen from the test sample and the antigen-chromophore or antigen-fluorophore conjugate to migrate multidirectionally between chamber 3 and 5 in a few minutes time. If antibody molecules of the IgG class are employed (m.w. approximately 150,000), then the m.w.c.o. of the membrane must be smaller than 150,000. In order to ensure that the antibody molecules do not migrate through, a membrane with a m.w.c.o. of 50,000 or 100,000 should be selected. When testing for small molecular weight substance, i.e., in the range of the hundreds or low thousands, this membrane would easily allow these smaller molecules to migrate multidirectionally through the membrane. When the individual shakes the apparatus, the smaller molecules migrate through the semipermeable membrane. The concentration of these small molecules on each side of the membrane is ultimately dependent on osmotic equilibrium. However, during the short duration of the assay, equilibrium is generally not reached. Once antigen molecules from the test sample pass from chamber 5 to chamber 3, another reaction occurs. Some of the antigen-chromophore (or antigen-fluorophore) conjugates become disassociated from the antibody molecules. Once one or two of the binding sites are exposed each of the antibody molecules, antigen from the test sample can bind to the antibody molecules. With greater concentrations of antigen molecules in the test sample, more will pass through the membrane; and more of these antigen molecules will displace the antigen-chromogen (or antigen-fluorophore) conjugates from the antibody molecules. After displacement occurs, the antigen-chromogen (or antigen-fluorophore) conjugates will migrate through the membrane. The end result of this migration is that chromophores (or fluorophores) will be present on both sides of the membrane (in both chambers 3 and 5). Thus, the solution on both sides of the membrane will appear colored showing a positive reaction as in FIG. 4B. At this stage, migration of molecules can be halted by reinserting the non-permeable barrier.

In order for all of the reactions to proceed properly, the correct concentrations of reagents must be employed. As with other immunoassay procedures, the concentration of each reagent must be carefully calibrated based on the expected range of concentrations for the test samples. Examples of calibration errors and the end result of these errors are given in the following paragraphs.

If there is an excess of antibody molecules in chamber 3, then all or most of the antigens from the test sample will be able to locate binding sites on the antibody molecules. In this case, few, if any, antigen-chromophore (or antigen-fluorophore) conjugates will be displaced; and these conjugates will not migrate to chamber 5 of the apparatus. The end result is that chamber 5 will appear to be relatively colorless. A test may then be interpreted as negative when it is indeed positive.

If an excess of antigen-chromogen (or antigen-fluorophore) conjugates is added to chamber 3 and a small number of antibody molecules are present, then these conjugates may not locate a sufficient number of antibody molecule binding sites. Thus, the conjugates will be free in solution; and the conjugates will migrate freely through the semipermeable membrane once it is exposed. This will occur whether or not there is antigen in the test sample. If migration occurs and there is no antigen in the test sample, then color will appear on both sides of the membrane and the reaction will be interpreted as positive when it is indeed negative.

In addition to the aforementioned reaction mechanism for the DITAM assay, alternate reaction mechanisms can be employed in the DITAM apparatus. Any additional alternate reaction mechanisms described hereinafter may also be employed to fit the needs of the user.

As another example of an exemplary reaction mechanism, an enzyme-substrate system may be used in place of the chromophore or fluorophore. If an enzyme is employed, then an extra step is added to the reaction. Since the enzyme-antigen conjugate is colorless, an individual is not able to visualize the presence of this molecule in either chamber, however, if the appropriate enzyme-substrate solution is added to chamber 5 of the apparatus, then the enzyme will degrade the substrate. For specific enzyme-substrate systems, the degraded substrate is colored. An example of such a system is: horseradish peroxidase as the enzyme and tetramethylbenzidine plus hydrogen peroxide as the enzyme substrate. In this case, the degraded substrate has a royal blue color. The intensity of the colored solution is dependent on the concentration of enzyme. If the reagents are properly calibrated, the color is ultimately dependent on the concentration of test sample antigen that was able to displace the antigen-enzyme conjugate. Enzyme-substrate systems will be discussed in greater detail hereinafter with another embodiment of the DITAM apparatus.

FIGS. 6A–6D and 7A–7C are diagrammatic representations of reaction sequences for another chemical reaction mechanism. In each case, the DITAM apparatus is used in conjunction with chemical vapor detecting equipment. In these reaction sequences, the antibody molecule is labeled with an enzyme. Labeled antigen is not required. Thus, one less reagent is needed for this assay. The reaction of enzyme with substrate produces vapors which leave the solution and can be detected with the appropriate equipment. These enzyme-substrates may, or may not, produce a color change.

The most important criteria in selecting an enzyme-substrate system is to ensure that the resulting products are highly volatile.

Figure 6A:
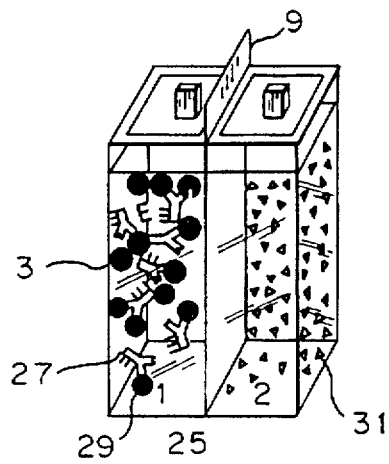
FIGS. 6a–6c show a diagrammatic representation of an exemplary reaction sequence when the absence of vapors indicates a positive reaction.
Figure 6B:
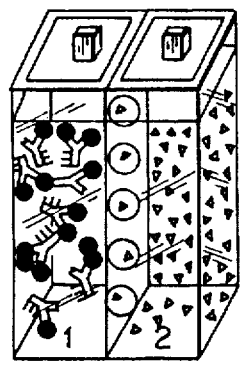
Figure 6C:
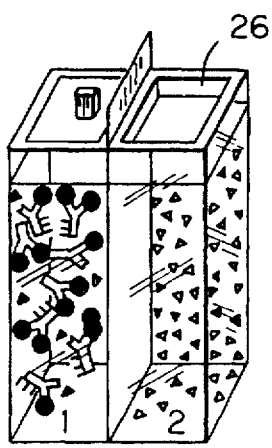

FIGS. 6A–6C is a diagrammatic representation of the reaction sequence that occurs when a test sample contains bacterial or fungal organisms and the DITAM apparatus and assay are to be used in conjunction with chemical vapor-detecting equipment or vapor detection by a user. In FIG. 6A, chamber 3 contains antibody molecules (Y-shaped structures in the diagram) 25 that are labeled with enzymes 27 (indicated by an E attached to each Y-shaped structure). When the test sample is added to chamber 3, bacteria or fungal organisms 29 (large dark spherical structures in the diagram) are introduced into chamber 3. When an individual shakes the apparatus for 1–2 minutes, enzyme-labeled antibodies bind to the bacterial or fungal organisms. This results in the formation of large molecular weight complexes. Chamber 5 contains an enzyme-substrate solution (the enzyme-substrate molecules 31 are drawn as small triangles).

The nonpermeable barrier 9 is removed by lifting upwards, and this exposes the semipermeable membrane. (FIG. 6B). For this assay, the membrane has a m.w.c.o. of 300,000. Other m.w.c.o. membranes can be used depending on the type of substance to be tested for. The individual shakes the apparatus in a forward and backward direction for 1 minute. The large molecular weight complexes are not able to migrate through the membrane and these complexes (including the bound enzyme molecules) remain in chamber 3. Thus, little or no enzyme is present in chamber 5 to react with the substrate; and volatile substances (vapors) are not produced for detection through opening 26 in chamber 5.

Any further migration of molecules is halted when the nonpermeable barrier 9 is replaced (FIG. 6C). Alternately, the enzyme-substrate solution may be added to chamber 5 after the non-permeable barrier 9 has been replaced (FIG. 6C). The cap 7 of chamber 5 is removed and vapor-detecting equipment (not shown) is employed to demonstrate that vapors are absent. The absence of vapors indicates a positive reaction (specific bacterial or fungal organisms were present in the test sample).

In an alternate reaction sequence to be described hereinafter, a large quantity of vapors indicates a positive test sample and a relatively small quantity of vapors indicates a negative test sample.

Figure 7A:
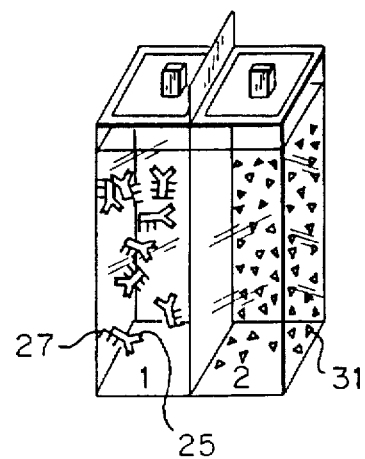
FIGS. 7a–7c show a diagrammatic representation of an exemplary reaction sequence when the presence of vapors indicates a negative reaction.
Figure 7B:
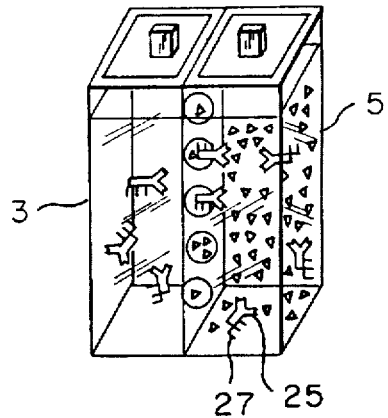
Figure 7C:
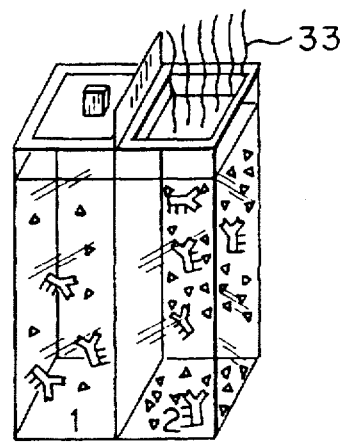
Figure 6D:
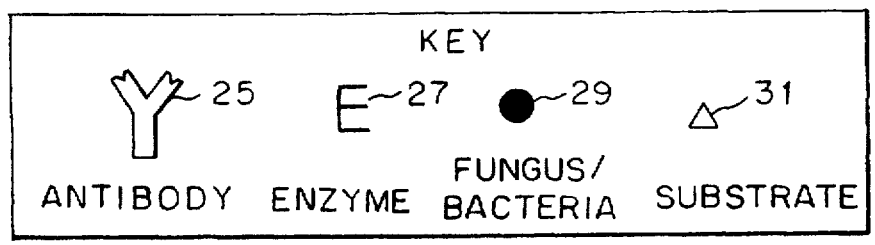
FIG. 6d illustrates a key for identifying substances in FIGS. 6a–6c and FIGS. 7a–7c.

FIGS. 7A–7C are a diagrammatic representation of the reaction sequence that occurs when a test sample does not contain bacterial or fungal organisms and the DITAM apparatus and assay are to be used in conjunction with chemical vapor-detecting equipment or vapor detection by a user. In FIG. 7A, chamber 3 contains antibody molecules 25 (Y-shaped structures in the diagram) that are labeled with enzymes 27 (indicated by an E attached to each Y-shaped structure). When the test sample is added to chamber 3, no bacterial or fungal organisms are introduced into chamber 3. When an individual shakes the apparatus for 1–2 minutes, enzyme-labeled antibodies do not have bacterial or fungal complexes to bind to; and no large molecular weight complexes are formed. Chamber 5 contains an enzyme-substrate solution (the enzyme-substrate molecules 31 are drawn as small triangles).

The nonpermeable barrier 9 is removed by lifting upwards, and this exposes the semipermeable membrane (FIG. 7B). For this assay, the membrane has a m.w.c.o. of 300,000. Other m.w.c.o. membranes can be used depending on the type of substance to be tested for. The individual shakes the apparatus in a forward and backward direction for 1 minute. The antibody-enzyme conjugate has a molecular weight of 218,000 and can migrate through the membrane. This size is based upon an antibody molecule with a molecular weight of approximately 150,000 and an enzyme molecule with a molecular weight of approximately 68,000. A variety of enzyme molecules can be bound to the antibody molecules. The only restriction is that the total molecular weight of the antibody-enzyme conjugate is small enough to pass through the semipermeable membrane. Enzyme-substrate is present in chamber 5 of the apparatus. When the enzyme reacts with the substrate in chamber 5, volatile substances (vapors) 33 are produced.

Any further migration of molecules is halted when the nonpermeable barrier 9 is replaced (FIG. 7C). The cap 7 of chamber 5 is removed and vapor-detecting equipment (not shown) is employed to demonstrate that vapors ar present. The presence of vapors 33 indicates a negative reaction (specific bacterial or fungal organisms were not present in the test 1 sample).

In an alternate reaction sequence to be described hereinafter, a large quantity of vapors indicates a positive test sample and a relatively small quantity of vapors indicates a negative test sample.

Figure 8:
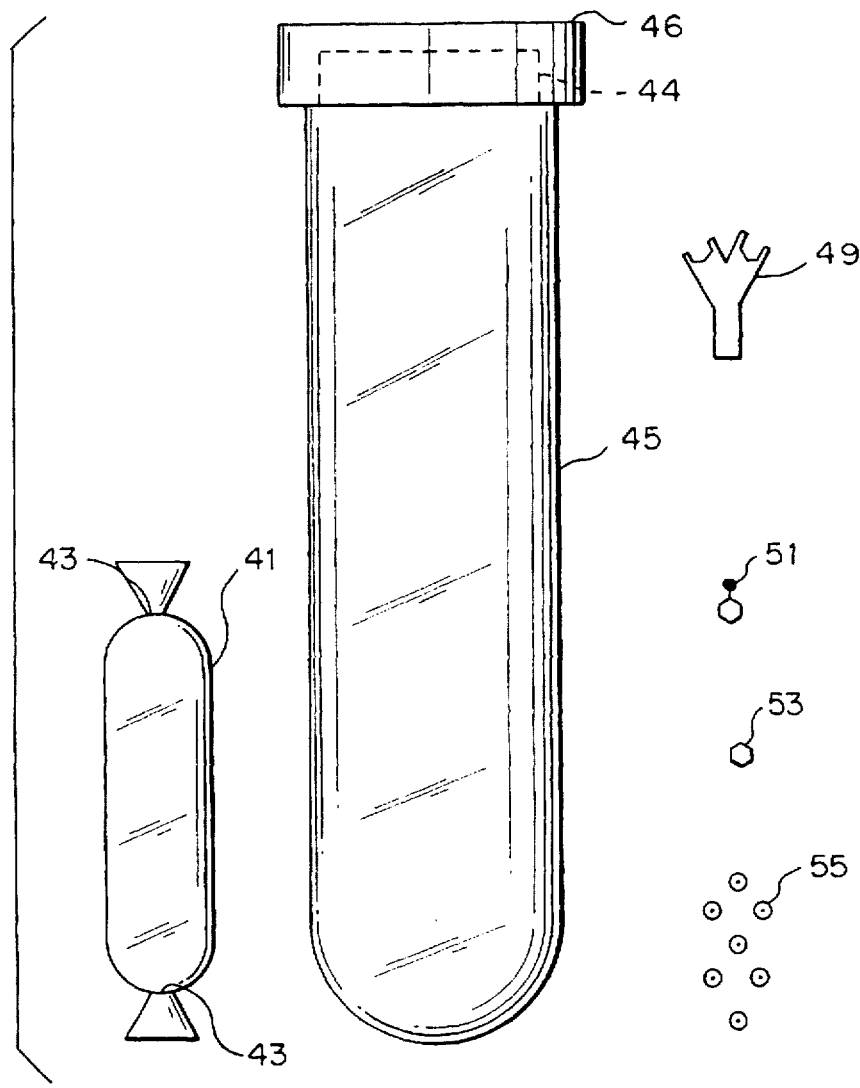
FIG. 8 shows a second embodiment of an unassembled assaying apparatus and a key identifying exemplary reagents for use in assaying.

In another aspect of the invention and with reference to FIG. 8, a second embodiment of the DITAM assay and apparatus 40 consists of a flexible, cylindrical semipermeable membrane (herein referred to as a "bag" 41) that is tied at both ends 43. The bag 41 is placed in a capped test tube 45 or an alternate pocket-sized vial. The size of the vessel can be varied to suit the needs of the user. For example, a 12 mm×75 mm polystyrene, round-bottom tube with a cap may be used as the reaction vessel may.

As with the DITAM apparatus described above, a variety of membranes can be employed; but dialysis-type membranes are the most useful. This is due to the fact that molecules can easily migrate through the membrane when an individual is gently shaking the apparatus from side to side. If other types of membranes are used, positive or negative pressure may be required for the molecules to traverse the membrane.

An advantage of the second embodiment of the DITAM apparatus is to increase the surface area of the membrane to enhance the rate of migration through the membrane. Again, all of the directions for performing the assay can be printed on the reaction vessel 45.

The reagents and supplies needed for performing a DITAM assay using the second embodiment are also shown in FIG. 8. The semipermeable membrane 41 and test tube 45 have been described above. The following reagents are placed inside the bag: specific antibody molecules 49, enzyme-labeled antigens 51, and a buffer solution or 0.85% saline. Since the membrane must be kept moist and the bag is difficult to reopen, reagents for this assay are not supplied in lyophilized form.

The selection of an enzyme substrate solution depends on the enzyme that is used to label the antigen. Several different enzyme-substrate systems may be employed. An example of one system follows: horseradish peroxidase for the enzyme and tetramethylbenzidine with hydrogen peroxide for the substrate. The vessel cap may be configured to house the enzyme-substrate solution as indicated by the hatched portion 44 in cap 46.

The test sample may contain the antigen (a molecule that is specifically recognized by the antibody molecule) or it may be devoid of antigen. The test sample may be liquid, i.e., contaminated water, saliva, serum or urine. Alternately, solid test samples, i.e., contaminated dust particles can be concentrated on cotton swabs and placed in test tubes along with a buffer solution. Again, these procedures apply to all embodiments of the invention.

FIGS. 9A–9C are diagrammatic representations of the reaction sequence for performing a DITAM assay using the second embodiment. The individual may fill the bag 41 with the appropriate test reagents or this bag 41 may be pre-filled by a manufacturer. If the bag is prefilled, only the following steps are required for the performance of a DITAM assay: A liquid test sample is added to a fill line marked on the tube, the tube is capped, and the individual shakes the tube for approximately two minutes. The enzyme substrate solution is added, and the tube is shaken again for approximately 1 minute. Then the individual observes the tube for a color change. The color of the reaction product varies depending on the enzyme and enzyme substrate utilized.

An absence of color change illustrates a negative reaction. Using the enzyme-substrate described above, a turquoise color illustrates a positive reaction due to the degradation of the substrate (tetramethylbenzidine plus hydrogen peroxide) by the enzyme (horseradish peroxidase). Other colored reaction products are possible depending on the enzyme-substrate system selected.

FIG. 9A illustrates the bag 41 inside the capped test tube 45. Using the key in FIG. 8 the bag contains antibody molecules 49 and enzyme-labeled antigens 51 in solution. The antibody molecules 49 are bound to the enzyme-labeled antigens 51. In FIG. 9B, the test sample is added to the tube. This sample is added to a fill line 47 marked on the tube. When shaking occurs, the small molecular weight molecules (the antigens 53 in the test sample) are able to pass through the semipermeable membrane and into the bag. This event is driven by osmosis due to the difference in the concentrations of this molecule on each side of the semipermeable membrane. Once inside the bag 41, the antigens 53 from the test sample can displace the antigen-enzyme conjugates 51 from the antibody molecules. A larger concentration of antigen in the test sample will result in a larger number of displacement reactions. The enzyme-antigen conjugates 51 used for this assay have relatively small molecular weights (compared to the antibody molecules) and are able to migrate from the inside of the bag 41 to the outside of the bag. Because of the large size, the antibody molecules 49 are not able to migrate through the membrane and must remain inside the bag. In FIG. 9C, the enzyme substrate in solution is added to the test tube. Any enzyme molecules outside of the bag can degrade the molecules in the substrate solution represented by the black circles 57. This degradation causes a color change and indicates a positive reaction by the degrade enzyme-substrate 57 as described above. In order to halt the migration of molecules through the membrane, the bag may be removed prior to the addition of the enzyme-substrate solution.

As with the DITAM assay shown in FIG. 1A, it is essential that one uses the correct concentration of assay reagents. Based on the reaction mechanism, an excessive number of antibody molecules inside the bag will essentially hold all or most of the antigen and enzyme-labeled antigen molecules inside the bag. When filling the bag with reagents, care must be exercised not to contaminate the exterior of the bag with any enzyme molecules.

In addition to the aforementioned reaction mechanism for the second embodiments of the DITAM assay, alternate reaction mechanisms can be employed and will be described hereinafter.

In another aspect of the invention, a third embodiment of the DITAM apparatus and assay facilitates the detection of large molecular weight substances such as proteinaceous antigens from infectious organisms, i.e., bacteria, fungi and parasitic organisms, antibodies directed against these organisms, and large molecular weight toxins from these organisms. The basic form of the apparatus utilizes a membrane with a higher m.w.c.o. than the membranes utilized for other versions of the DITAM apparatus. For the third embodiment to be used for the detection of small molecular weight substances, a membrane with a lower m.w.c.o. is used.

Figure 10A:
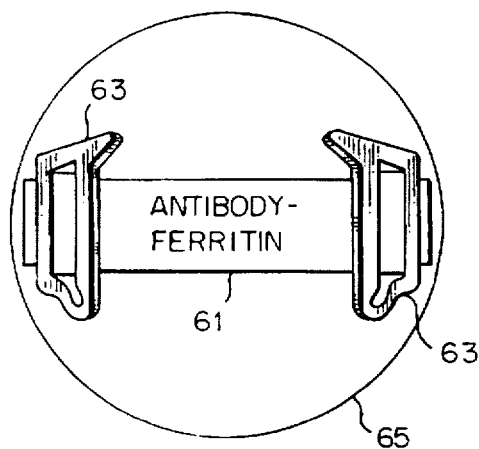
FIGS. 10a and 10b show another embodiment of the inventive assaying apparatus along with a diagrammatic representation of an exemplary reagent for use in assaying.

The third embodiment of the DITAM apparatus comprises a tubular semipermeable membrane 61 (herein referred to as a bag) closed at opposite ends by clamps 63. (FIG. 10A).

The bag 61 (filled with reagents) is placed in a Petri dish 65 or small vial or other reaction vessel. A wide variety of containers may be used such as a 7 dram snap-cap vial. A 15 dram snap-cap vial (or larger) may also be used if larger sample volumes are tested. The snap-cap vessel can be replaced by a 1 oz. (30 ml) screw-cap vessel or a larger size screw-cap vessel. A variety of other types of vessels may be utilized. The limiting factors in selecting any reaction vessel are size, optical clarity, and lack of reactivity with the reagents used in the assay. All of the chemical reactions are conducted in this vessel. The vessel must be large enough to accommodate the two clamps 63, the semipermeable membrane 61 and the total volumes of the test sample and the enzyme-substrate solution. The vessel may be configured to enable the storage of the enzyme-substrate solution in the cap as described above. All of the instructions for the assay can be printed on the side or top of the reaction vessel.

Since the third embodiment of the invention utilizes a somewhat brittle and stiff membrane that must be kept moist, clamps are used to secure both ends of the membrane. FIG. 10A illustrates the use of Spectra/Por® closures for use with membrane tubing sizes to 15 mm. Spectra/Por® Closures for use with membrane tubing sizes to 35 mm can also be used. A variety of other types of clamps may be used to seal the membrane at both ends. Ideally, clamps should only be used once. However, if clamps are to be reused, they must be carefully cleaned to remove any traces of enzyme. The latter could result in false positive reaction. Heat sealing at both ends of the membrane may also be an option. This would eliminate the need for clamps.

In this embodiment, the DITAM assay produces a color change in the reaction solution. This can be viewed with the unaided eye. To increase assay sensitivity, a small portable spectrophotometric device may be used to detect the color change produced by the reaction of enzyme with enzyme-substrate. In another variation of the DITAM assay, the reaction of enzyme with enzyme-substrate produces vapors which can be detected with chemical vapor-detecting equipment or a user of the apparatus.

Figure 10B:
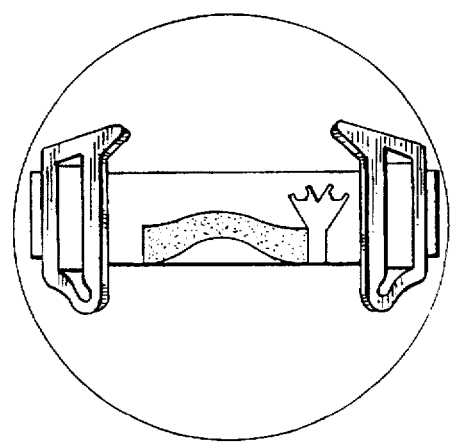

FIGS. 10A and 10B illustrate the use of an antibody-ferritin conjugate for this embodiment of the DITAM assay. FIG. 10B shows in schematic form an antibody represented by the Y-shaped structure bonded to a ferritin to form the antibody-ferritin conjugate.

Figure 11A:
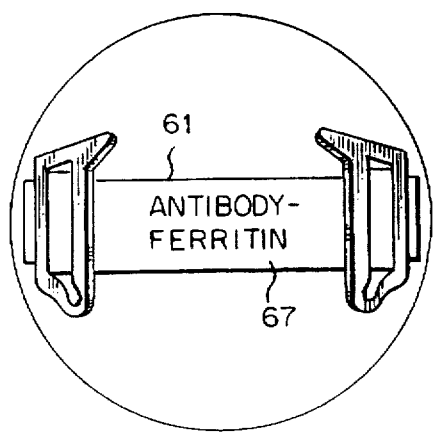

FIGS. 11A to 11D illustrate competitive reactions (antigen and enzyme-labelled antigen compete for binding sites on antibody molecules). The bag 61 has therein an antibody-ferritin conjugate (FIG. 11A). The conjugate has a substantially larger molecular weight than the antigens in a test sample. Thus, the conjugate is not able to pass through the pores of the membrane. This type of reaction is used for the detection of proteins from bacterial or fungal organisms.

The third embodiment of the DITAM assay can use the following reagents: antibody-ferritin conjugate, antigen-enzyme conjugate, antigen from the test sample, the enzyme-substrate solution and a buffer solution or 0.85% saline (FIGS. 11A–11D). The antibody-ferritin conjugate can be replaced with any antibody-X conjugate (where X is a large molecular weight substance that prohibits the conjugate from migrating through the pores in the membrane). Examples include: antibody-microspheres and antibody-colloidal gold.

In another variation of the DITAM assay, the following reagents are used: antibody-enzyme conjugate antigen from test sample (where the antigen is a bacterial or fungal organism), the enzyme-substrate solution, and a buffer solution or 0.85% saline. These are illustrated in FIGS. 13A–13C and 15A–15D.

As with the other embodiments of the DITAM assay, reagent concentrations must be carefully calibrated. Incorrect concentrations may result in testing errors such as false positives. Also, any contamination of the exterior of the bag or the clamps with enzyme prior to testing will result in false positive results.

The test sample may be a liquid, i.e., contaminated water, saliva, serum or urine. Alternately, solid test samples, i.e., contaminated dust particles can be concentrated on cotton swabs and placed in test tubes along with a buffer solution.

Figure 11B:
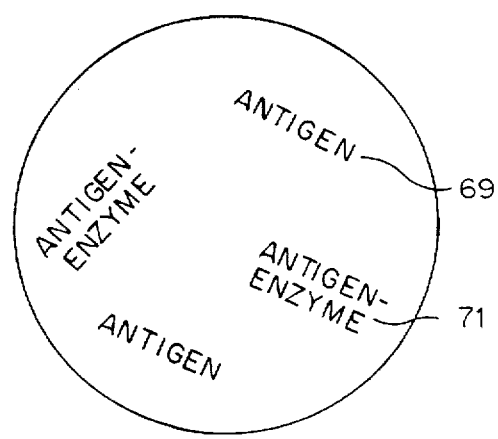
Figure 11C:
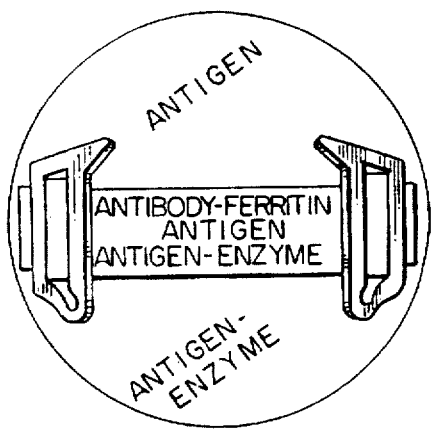
Figure 11D:
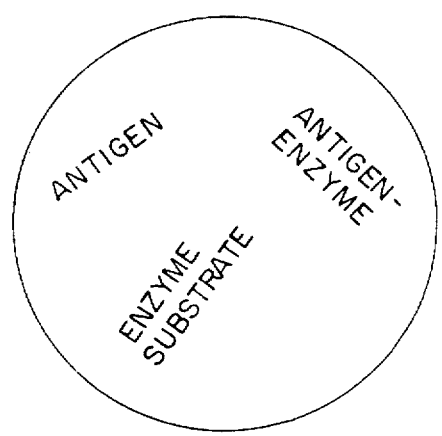
Figure 12:
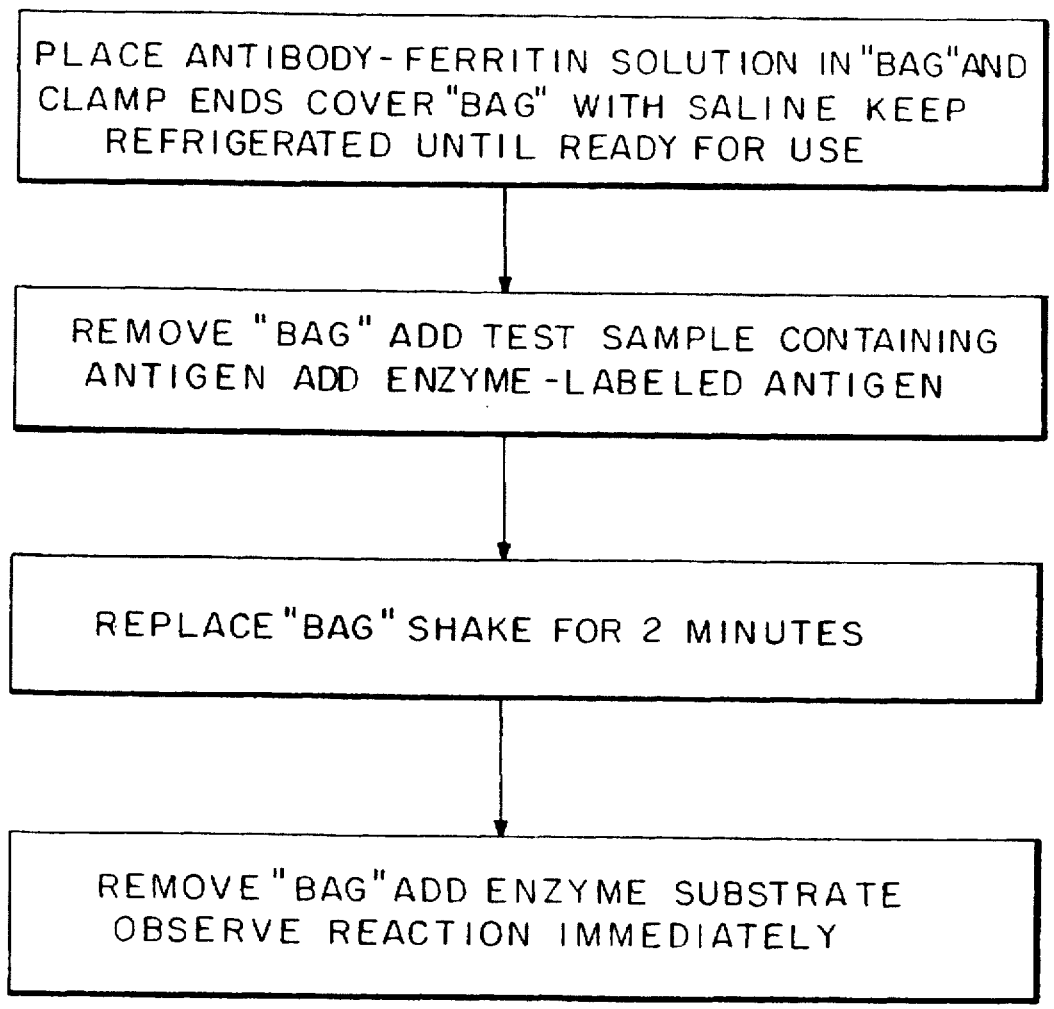
FIG. 12 is a flowchart describing the reaction sequence steps for FIGS. 11a–11d.

FIGS. 11A–11D and 12 are diagrammatic representations of the reaction sequence for the third embodiment of the DITAM assay. In order to perform this assay, the tubular semipermeable membrane 61 (bag) is clamped at one end. The antibody-ferritin solution 67 is pipetted into the bag and the bag is clamped at the other end (FIG. 11A). The solution appears brownish in color due to the ferritin. The bag 61 is then placed in a reaction vessel and covered with a buffer solution or 0.85% saline to keep the membrane moist. Long-term storage may require the addition of an additive to enhance stability and halt or slow the growth of any contaminants such as bacterial and fungal organisms. Storage at 4° C. is also recommended if the assay is not performed shortly after filling the bag. To continue with the assay, the bag 61 is removed from the reaction vessel (FIG. 11B). The test sample 69 (which may contain antigen) and a solution of enzyme-labeled antigen 71 are added to the reaction vessel. The bag 61 is then placed in the reaction vessel again, and the individual shakes the vessel for approximately 2 minutes (FIG. 11C). Afterwards, the bag 61 is removed again. The enzyme-substrate solution is added to the reaction vessel and the individual observes the vessel for a color change in the reaction solution (FIG. 11D). Using horseradish peroxidase as an enzyme and tetramethylbenzidine with hydrogen peroxide as the enzyme-substrate solution, the positive reaction solution is turquoise or yellow-gold in color. The color and the intensity of the color are, dependent on the concentration of enzyme in the solution. In turn, the concentration of enzyme in the solution can be used to determine the initial concentration of antigen in the test sample. Thus, the greater the color intensity, the greater the concentration of antigen in the initial test sample. A negative reaction is clear.

Figure 13A:
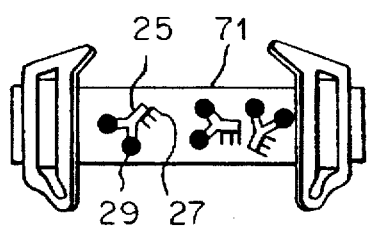
FIGS. 13a–13c show a diagrammatic representation of a reaction sequence when the absence of vapors indicates a positive reaction.
Figure 13B:
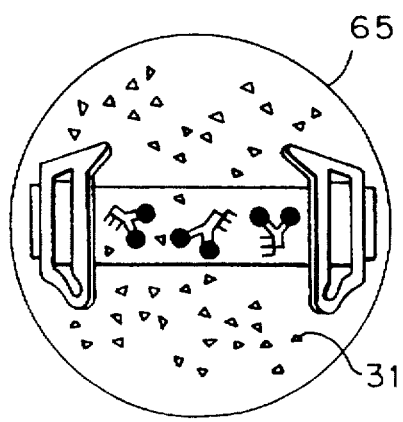
Figure 13C:
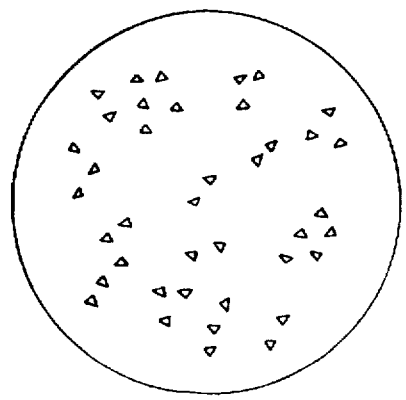

Another use of the third embodiment of the DITAM assay uses chemical vapor-detecting equipment or vapor detection by a user. With reference to FIGS. 6D, 13A–13C and 14, the tubular semipermeable membrane 61 (bag) is clamped at one end. The antibody-enzyme conjugate 71 (illustrated by a Y-shaped structure with an E attached 27) is pipetted into the bag along with the test sample. The test sample contains bacteria or fungi (illustrated by dark-circular structures). The bag 61 is clamped at the other end, and it is shaken for 1–2 minutes. To do this, the bag 61 may be placed in a small container. Alternatively, the bag may be inverted many times. The bag is then placed in a reaction vessel 65, i.e. a Petri dish or other appropriate container, which contains enzyme substrate solution (illustrated by triangular structures 31) (FIG. 13B). The reaction vessel is shaken for approximately 1 minute. Afterwards, the bag 61 is removed from the reaction vessel (FIG. 13C). Vapor-detecting equipment (not shown) can be used to demonstrate that vapors are absent (a positive test sample as- shown in FIG. 13C). For a negative test sample, vapors would be present.

Figure 15A:
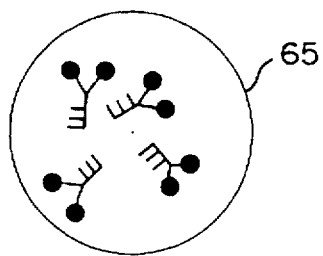
FIGS. 15a–15d show another diagrammatic sequence of a reaction scheme when the presence of greater concentrations of vapors indicates a positive reaction.
Figure 15B:
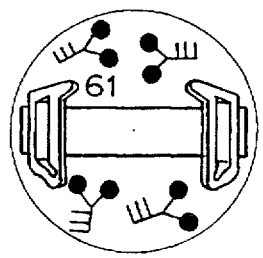
Figure 15C:
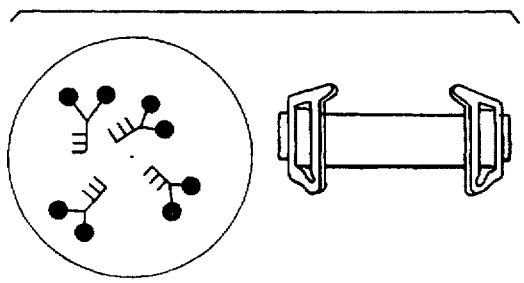
Figure 15D:
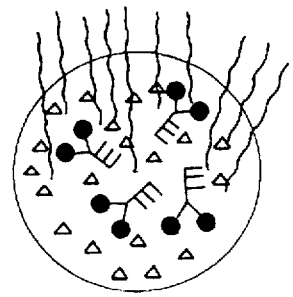
Figure 16:
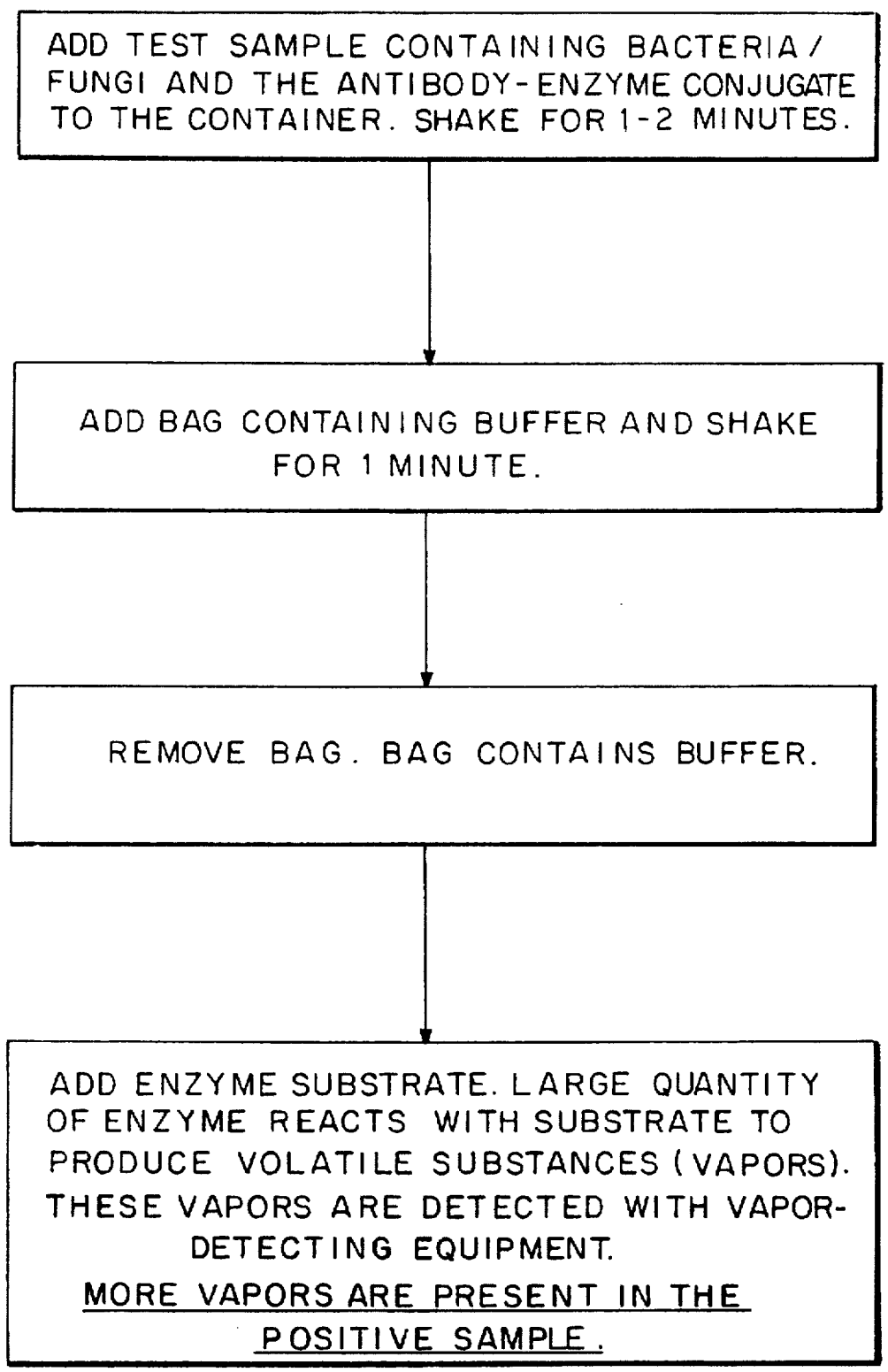
FIG. 16 is a flowchart describing the reaction sequence for FIGS. 15a–15d.
Figure 18:
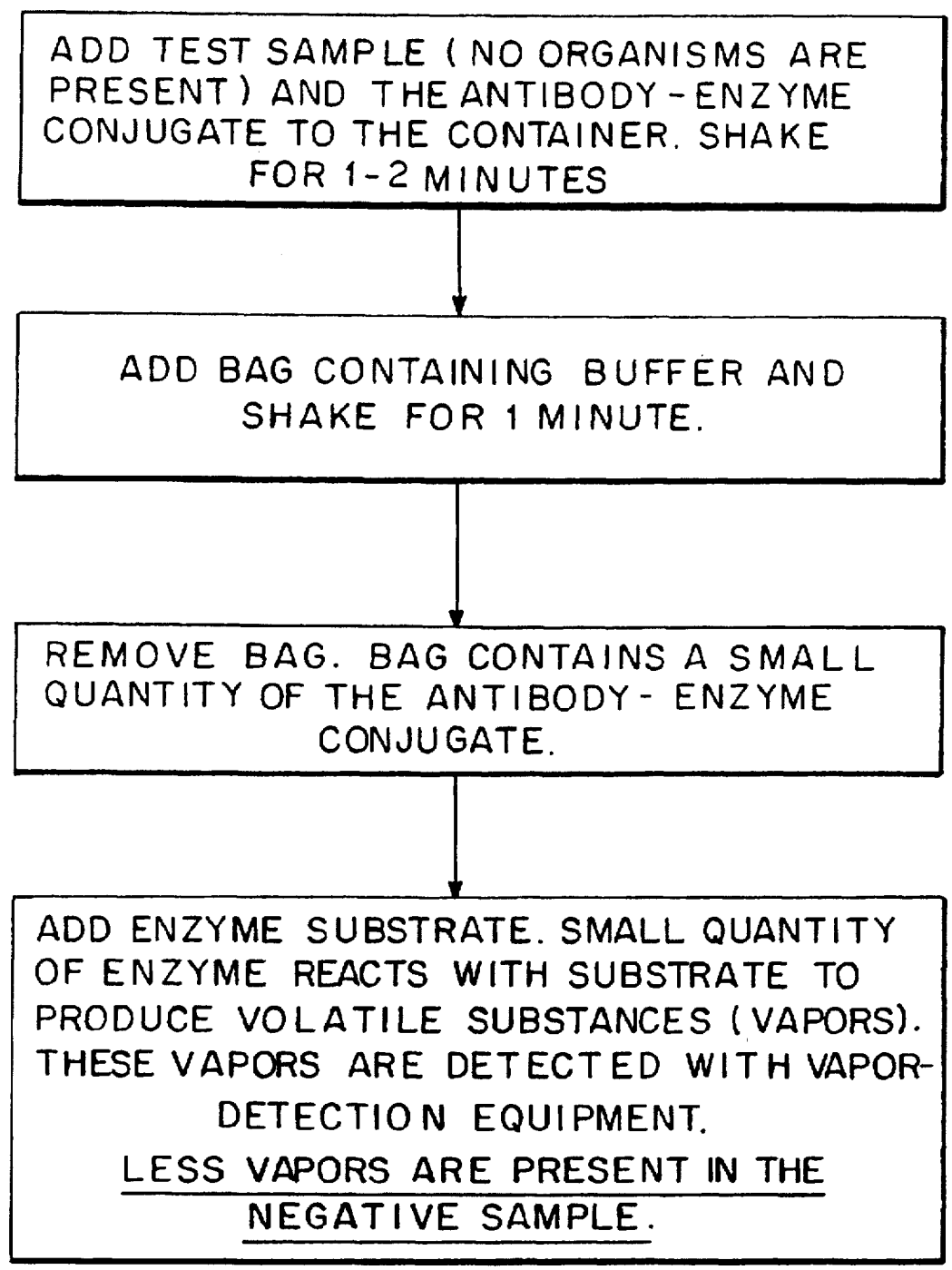
FIG. 18 is a flowchart describing the reaction sequence steps for FIGS. 17a–17d.

FIGS. 15A–15D, 16, 17A–17D and 18 also illustrate the DITAM apparatus and assay for use with chemical vapor-detecting equipment. Unlike FIGS. 13A–13C and 14, the DITAM assay procedures have been altered slightly so that the presence of more vapors indicates a positive reaction and less vapors indicates a negative reaction. This variation permits ease of interpreting reaction results. In FIGS. 15A and 17A, the test sample and the antibody-enzyme conjugates 71 are added to the reaction vessel 65. This vessel is shaken for 1–2 minutes. The bag 61 (a semipermeable membrane containing buffer and clamped at both ends) is added to the reaction vessel (FIGS. 15B and 17B). After shaking the reaction vessel for 1 minute, the bag 61 is removed (FIGS. 15C and 17C). Enzyme substrate solution is added to the reaction vessel, and vapor-detecting equipment is used to determine the amount of vapors present (FIGS. 15D and 17D).

Using the third embodiment of the DITAM assay, either competitive reactions or displacement reactions may be carried out. For the competitive reaction, neither the antigen or the enzyme-labeled antigen are bound to antibody molecules at the beginning of the assay. Both the antigen and the enzyme-labeled antigen are outside the bag at the beginning of the assay (FIG. 11A). During the shaking step, the antigen and the enzyme labeled antigen can migrate through the pores of the membrane. The antibody-ferritin conjugate is too large to migrate through the pores of the membrane, and it is retained within the bag 61 (FIG. 11C). Both the antigen and the enzyme-labeled antigen have approximately equal chances of migrating through the semipermeable membrane, locating the antibody molecules, and binding to the antibody molecules. When the bag is removed from the reaction vessel, a portion of the antigen and enzyme-labeled antigens are removed along with the bag. With increasing concentrations of antigen in the test sample, a larger percentage of binding sites on the antibody-ferritin conjugates are filled by the antigen. Thus, fewer sites are occupied by the enzyme-labeled antigen. These unbound enzyme-labeled antigens can easily migrate through the pores of the semipermeable membrane. Thus, with increasing concentrations of antigen in the test sample, the concentration of enzyme-labeled antigen outside of the bag will also increase. When the bag is removed, there will be larger concentrations of enzyme-labeled antigen in the vessel to react with the enzyme substrate solution. The color and intensity of the reaction solution is proportional to the concentration of enzyme-labeled antigen. In turn, this can be related back to the concentration of enzyme-labeled antigen. In turn, this can be related back to the concentration of antigen in the test sample.

For displacement reactions, e.g. FIGS. 9A–9C, the enzyme-labeled antigen would be placed in the bag along with the antibody-ferritin conjugate at the beginning of the assay. These enzyme-labeled antigens are able to bind to the antibody-ferritin molecules in the bag. When the test sample is placed in the reaction vessel (outside of the bag), the antigens in the test sample must migrate through the pores of the semipermeable membrane, locate antibody molecules inside the bag, displace some of the enzyme-labeled antigens from their binding sites on the antibody-ferritin molecules, and finally bind to the antibody-ferritin molecules. The enzyme-labeled antigens are then free to migrate through the pores of the semipermeable membrane to the solution outside of the bag.

The competitive reactions and displacement reactions described above are for use with enzyme-labeled antigens and enzyme substrates. In both cases, positive or negative test samples are determined by a change in the color of the reaction solution.

When using chemical vapor-detecting equipment, the reaction solution does not change color. However, the presence or absence of vapors is an indication of whether or not the test sample was positive or negative. In FIG. 13A, the bag is filled with antibody-enzyme conjugates and the test sample. The test sample containsbacteria or fungi which bind to the antibody-enzyme conjugates during the shaking step. The bag is then placed in a reaction vessel which contains enzyme substrate solution (FIG. 13B). The large complexes are not able to migrate through the pores of the semipermeable membrane. Thus, little, if any, enzyme is present in the enzyme-substrate solution when the bag is removed from the reaction vessel. Vapors are not produced. When there are no bacterial or fungal organisms in the test sample to bind to the antibody-enzyme conjugate, this conjugate is small enough to pass through the pores of the semipermeable membrane. When the bag is removed from the reaction vessel, antibody-enzyme conjugates are present in the enzyme-substrate solution. When the enzyme reacts with the enzyme-substrate solution, vapors are produced. Vapor-detecting equipment can be used to detect these vapors. For this reaction mechanism, the presence of vapors indicates that the test sample did not contain specific bacterial or fungal organisms.

The DITAM assay represented in FIGS. 15A–15D, 16, 17A–17D and 18 also utilize chemical vapor-detecting equipment. Because of the variation in the reaction mechanism for these assays, the presence of more vapors indicates a positive test sample and less vapors indicates a negative test sample (FIGS. 15A and 17A).

The test sample and the antibody-enzyme conjugates are added to the reaction vessel. During the shaking step, bacterial or fungal organisms bind to antibody-enzyme conjugates to form large complexes. When the bag is added to the reaction vessel and shaken for 1 minute, some of the antibody-enzyme conjugates pass through the pores of the semipermeable membrane. Large complexes are not able to migrate through the pores of the semipermeable due to their large sizes. When the bag is removed from the reaction vessel, it either contains buffer or buffer plus a small quantity of the antibody-enzyme conjugates (FIGS. 15B, 15C, 17B and 17C). The enzyme substrate solution is added to the reaction vessel, and vapor-detecting equipment is used to determine the amount of vapors present. In FIG. 15D, the large quantity of enzyme in the vessel reacts with the enzyme-substrate to produce volatile substances (vapors). The larger amount of vapors indicates that the test sample was positive (specific bacteria or fungal organisms were present in the test sample). In FIG. 17D, the small quantity of enzyme in the vessel reacts with the enzyme-substrate to produce volatile substances (vapors). The smaller amount of vapors indicates that the test sample was negative (no specific bacteria or fungal organisms were present in the test sample). The appropriate concentrations of reagents must be used for this assay, and the assay must be carefully calibrated in order to determine the amount of vapors that are representative of negative reactions and the amount of vapors that are representative of positive reactions.

Although a primary assay reaction mechanism has been disclosed for each embodiment of the DITAM apparatus, it should be understood that because of the versatility of the invention, many alternate assay reaction mechanism may be employed to suit a user's needs. Thus, the assay has utility for a greater number of users and for a greater number of applications.

As stated above, a wide variety of membranes may be selected for use in each embodiment of the DITAM apparatus. The selection of membranes is intended to suit the needs of a user. The following provides a listing of several types of membranes that may be used to construct the different versions of the DITAM apparatus. All of these membranes are from a single manufacturer, and they are listed here for illustration purposes only. Membranes produced by other manufacturers can also be used to construct DITAM apparatuses.

All of the membranes in the following listing are from Spectrum Medical Industries, Inc. 60916 Terminal Annex, Los Angeles, Calif., 90060. The membrane types are provided for the sole purpose of providing examples of membranes that may be used in the DITAM apparatus. Examples of membranes includes (1) SPECTRAPOR® Membrane tubing with any one of the following m.w.c.o.'s: 3,500, 6,000–8,000, 12,000–14,000, (2) Spectra/Por® Membrane tubing with a m.w.c.o. of 50,000, and (3) Spectra/Por® Molecularporous Membrane tubing and Spectra/Por® CE Molecularporous Membrane tubing with any one of the following m.w.c.o.'s: 25,000, 50,000, 100,000, 300,000, and 500,000. The choice of m.w.c.o. depends on the type of substance to be tested for. Spectrum Medical Industries, Inc., the manufacturer, describes the Spectra/Por® Molecularporous Membrane and Spectra/Por® CE Molecularporous Membrane tubing as nonprotein binding cellulose esters. They are sensitive to organic solvents, high temperatures, and should not be allowed to dry. SPECTRAPOR® Membrane tubing type (1) above is supplied by the manufacturer in a "dry" form while types (2) and (3) above are supplied by the manufacturer is "moist" form (in a 0.05% sodium azide solution). For these membranes, moisture is a critical factor in performance. Thus, the membrane must be kept moist in order to ensure optimal performance in the DITAM apparatus and assays. For prolonged periods of time, the membranes in the DITAM apparatus can be kept "wet" in a 0.05% sodium azide solution until the DITAM apparatus are employed. At that time, the solutions may be discarded and replaced with the test solution. If the presence of 0.05% sodium azide interferes with the DITAM assay, then the interior of the apparatus may be washed with a buffer solution or 0.85% saline solution prior to use.

The aforementioned membranes are available from the manufacturer in different flat widths and cylinder diameters. Membranes with a flat width of 12 mm (cylinder diameter of 7.5 mm) and a flat width of 34 mm (cylinder diameter of 21.6 mm) may be employed in the DITAM apparatus. A variety of sizes can be employed to suit the needs of the end user.

Additional equipment may be required to increase the sensitivity of the assay or to give a quantitative result rather than a qualitative result for the assay. Optical density detectors, small spectrophotometers, and chemical-vapor detecting equipment have been mentioned previously. The type of detector will depend on the type of reagents and reactions for each DITAM assay. Since these detectors are well known in the art, further description is not provided.

Although reagents useful for performing the various DITAM assays have been disclosed above, other reagents may serve as alternatives. Antigens may be labeled with chromophores, fluorophores, enzymes that produce colored compounds upon reaction with the appropriate substrates, enzymes that produce highly volatile substances (vapors) upon reaction with the appropriate substrates, iron-containing molecules, radioactive substances, or any other molecule that can be bound to the antigen and utilized as a signal that a reaction has occurred.

Figure 19:
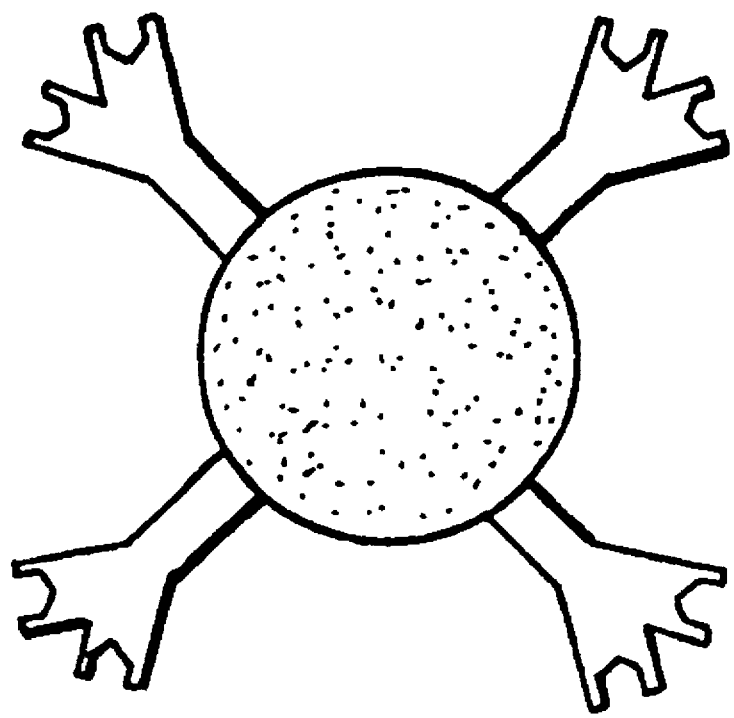
FIG. 19 shows a conjugate comprising antibodies bound to ferritin, microspheres, or colloidal gold.

Either monoclonal or polyclonal antibodies can be used for the DITAM assay. If a single substance is to be detected, then antibodies with a single specificity would be selected. However, if multiple substances must be screened for in a single DITAM assay, then several different batches of antibodies (each having a different specificity) would be selected. When testing for small molecular weight substances, antibodies of the IgG Class may be utilized without further alteration. When testing for large molecular weight substances, antibodies of the IgG class can be conjugated to ferritin or to microspheres or to colloidal gold (FIG. 19) or a wide variety of other large molecules. These molecules should not restrict the activity of the antibody molecules and they should have a size that is large enough to prohibit the antibody-large molecule complex from migrating through the pores in the DITAM apparatus. Alternatively, antibodies of the IgM Class may be employed since they are substantially larger in size than antibodies of the IgG Class.

For DITAM assays requiring chemical vapor-detection equipment, the antibodies can be labeled with any of a wide variety of enzymes that will react with the appropriate substrate to produce volatile substance (vapors). The selection of enzyme depends on the type of vapor-detection equipment and the needs of the end user.

Receptor molecules may be used as a replacement for antibody molecules in any of the DITAM assays. In either instance, the recognition molecule must be capable of binding to the specific substance of interest (analyte) in the test sample. In addition, the type of chemical bond must be weak enough to enable association and disassociation reactions to occur. Thus, an analyte in a test sample can displace a labeled-analyte that is bound to the receptor molecule. Unbound analyte molecules (either labeled or unlabeled) can easily pass through the pores of the semipermeable membrane (bag).

For the various embodiments of the DITAM apparatus and assays, directions for performing each type of assay have been disclosed. Due to the versatility of the DITAM assay, other variations in assay procedures are possible. Examples of two of these variations follows. Both involve competitive-type antigen-antibody reactions. The first variation is for the detection of small molecular weight substances, and the second variation is for the detection of large molecular weight substances.

In order to detect small molecular weight substances, an individual places a known quantity of specific antibodies and enzyme-labeled antigens in the reaction container. The test sample, which contains an unknown quantity of antigen, is also placed in the reaction vessel. The enzyme may be substituted with another molecule as described above. The container size depends on the use's needs. The vessel is shaken for approximately 2 minutes. A bag (as described previously) is placed in the reaction vessel. The molecular weight cutoff of the bag will depend on the substance to be tested for. The bag contains either a buffer solution or 0.85% saline. Alternatively, the bag contains the same type of specific antibody molecules that have been added to the solution in the reaction vessel. The reaction vessel is shaken for approximately 1–2 minutes. Then the bag is removed. Enzyme substrate is added to the reaction vessel. The individual observes the color of the solution in the reaction vessel. Ideally, a small spectrophotometer should be used to product a quantitative result. In addition to the test sample, negative and positive control samples should be tested for comparison purposes. A decrease in color and intensity in the reaction solutions indicates an increase in the amount of antigen in the test sample. Thus, the color of the control solutions should be compared to the color of the test solution.

In order to detect large molecular weight substances, an individual places a known quantity of specific antibody molecules (bound to large molecular weight substances such as ferritin) and enzyme-labeled antigens in the reaction vessel. The test sample, which contains an unknown quantity of antigen, is also placed in the reaction vessel. The enzyme may be substituted with another molecule as described above. The container size depends on the user's needs. The vessel is shaken for approximately 2 minutes. A bag (as described previously) is placed in the reaction vessel. The molecular weight cutoff of the bag will depend on the substance to be tested for. The bag contains either a buffer solution or 0.85% saline. Alternatively, the bag contains the same type of specific antibody molecules (bound to large molecular weight substances such as ferritin) that have been added to the solution in the reaction vessel. The reaction vessel is shaken for approximately 1–2 minutes. Then the bag is removed. Enzyme substrate is added to the reaction vessel. The individual observes the color of the solution in the reaction vessel. Ideally, a small spectrophotometer should be used to produce a quantitative result. In addition to the test sample, negative and positive control samples must be tested for comparison purposes. A decrease in color and intensity in the reaction solutions indicates an increase in the amount of antigen in the test sample. Thus, the color of the control solutions should be compared to the color of the test solution.

For both of the aforementioned variations in the DITAM assay, antigen molecules from the test sample compete with enzyme-labeled antigens for binding sites on the specific antibody molecules. This occurs during the first shaking step. With increasing concentrations of antigen in the test sample, more binding sites on the antibodies will be filled by these antigens; and fewer binding sites on the antibody molecules will be filled by the enzyme-labeled antigens. When the bag (semipermeable membrane) is added to the reaction vessel, unbound antigen and unbound enzyme-labeled antigen molecules freely pass through the pores of the membrane. This occurs during the second shaking step. The antibody molecules or antibody molecules bound to large molecular weight substances are not able to pass through the membrane due to their sizes. When the bag is removed from the reaction vessel, the antigens and enzyme-labeled antigens inside the bag are also removed. With the removal of a substantial number of enzyme-labeled antigen molecules when the bag is removed, there will be fewer enzyme-labeled antigen molecules in the reaction vessel to react with the enzyme-substrate solution and produce a color change. Thus, with increasing concentrations of antigen in the test sample, the color of the reaction solution will decrease in intensity.

When specific antibody molecules or specific antibody molecules (bound to large molecular weight substances such as ferritin) are contained with the bag, antigens and enzyme-labeled antigens will bind to these antibodies. This may prevent or slow down the rate of migration of these small molecules from the inside to the outside of the bag. Thus, better results could be achieved.

As such, an invention has been disclosed in terms of preferred embodiments thereof which fulfill each and every one of the objects of the present invention as set forth hereinabove and provides an improved assaying apparatus and method for detecting a wide range of molecular weight substances.

Of course, various changes, modifications and alternations from the teachings of the present invention may be contemplated by those skilled in the art without departing from the intended spirit and scope thereof. Accordingly, it is intended that the present invention only be limited by the terms of the appended claims.

I claim:

1. A rapid method for competitive displacement immunoassays characterized by diffusion through a membrane to separate free tagged analyte from bound tagged analyte to detect an analyte in the form of antigens contained in substances selected from the group consisting of hazardous wastes, pesticides, toxic chemicals, chemical warfare agents and infectious organisms, said method comprising the steps of:

(1) assembling a detection device having (A) reagents for performing said immunoassay comprising tagged analyte-antibody complexes and (B) a multi-chambered container having a semi-permeable membrane secured between chambers, the semi-permeable membrane having a predetermined molecular weight cut off to allow diffusion between chambers of analyte and tagged analyte and to prevent passage between chambers of analyte-antibody complexes and tagged analyte-antibody complexes, said reagents having predetermined analyte binding characteristics to effect indirect detection of the analyte, said reagents being distributed in one or more alternating chambers, said adjacent chambers having a removable nonpermeable barrier adjacent to the semipermeable membrane wherein fluid communication between adjacent chambers is controlled by removal or insertion of said nonpermeable barrier, (2) processing a sample of suspected analyte in the detection device by measuring for the presence or absence of free tagged analyte and correlating the tagged analyte with the predetermined binding characteristics of the reagents, and (3) determining whether the analyte is present.

2. The method of claim 1 wherein the tagged analyte-antibody complexes are tagged with a chromogen or a fluorophore.

3. The method of claim 2 wherein the tagged analyte antibody complexes are tagged with a chromogen.

4. The method of claim 2 wherein the tagged analyte-antibody complexes are tagged with a fluorophore.

5. The method of claim 1 wherein the molecular weight cut off is in the range of 3,500 to 500,000 daltons.

* * * * *